US008709383B2

(12) United States Patent
Scherman et al.

(10) Patent No.: US 8,709,383 B2

(45) Date of Patent: Apr. 29, 2014

(54) PERSISTENT LUMINESCENCE NANOPARTICLES USED IN THE FORM OF A DIAGNOSIS AGENT FOR IN VIVO OPTICAL IMAGING

(75) Inventors: Daniel Scherman, Paris (FR); Michel Bessodes, Villejuif (FR); Corinne Chaneac, Bagnolet (FR); Didier Louis Gourier, Paris (FR); Jean-Pierre Jolivet, Vaugrigneuse (FR); Quentin Le Masne De Chermont, Paris (FR); Serge Maitrejean, Paris (FR); Fabienne Sylvie Pelle, Colombes (FR)

(73) Assignees: Centre National de la Recherche Scientifique (CNRS), Paris (FR); Institute National de la Sante et de la Recherche Medicale (INSERM), Paris (FR)

( * ) Notice: Subject to any disclaimer, the term of this patent is extended or adjusted under 35 U.S.C. 154(b) by 990 days.

(21) Appl. No.: 12/091,571

(22) PCT Filed: Oct. 30, 2006

(86) PCT No.: PCT/EP2006/067950

§ 371 (c)(1), (2), (4) Date: Aug. 28, 2008

(87) PCT Pub. No.: WO2007/048856

PCT Pub. Date: May 3, 2007

(65) Prior Publication Data

US 2009/0155173 A1 Jun. 18, 2009

(30) Foreign Application Priority Data

Oct. 28, 2005 (FR) ..................................... 05 11113

(51) Int. Cl.
*A61K 49/00* (2006.01)

(52) U.S. Cl.
USPC ............................................... 424/9.1; 435/4

(58) Field of Classification Search
None
See application file for complete search history.

(56) References Cited

U.S. PATENT DOCUMENTS

| | | | | |
|---|---|---|---|---|
| 6,537,829 | B1 | 3/2003 | Zarline et al. | |
| 2003/0032192 | A1 * | 2/2003 | Haubold et al. | 436/56 |
| 2003/0059635 | A1 | 3/2003 | Naasani | |
| 2003/0180780 | A1 | 9/2003 | Feng et al. | |
| 2004/0014060 | A1 | 1/2004 | Hoheisel et al. | |
| 2005/0020922 | A1 * | 1/2005 | Frangioni et al. | 600/473 |
| 2005/0136258 | A1 | 6/2005 | Nie et al. | |
| 2007/0087195 | A1 * | 4/2007 | Meyer et al. | 428/403 |
| 2007/0218049 | A1 * | 9/2007 | Chen et al. | 424/130.1 |

OTHER PUBLICATIONS

Wang et al. Journal of Luminescence 2003, 34-37.*
Mehta et al., "Size-correlated spectroscopy and imaging of rare-earth-doped nanocrystals," *Applied Optics*, Apr. 20, 2003, vol. 42, No. 12, pp. 2132-2139.
Blasse et al., *Luminescent materials*, Chapter 5, 1994, Springer-Verlag, Berlin, pp. 91-107.
Jiang et al., "Luminescent properties of $CaMgSi_2O_6$-based phosphors co-doped with different rare earth ions," *Journal of Alloys and Compounds*, 2004, vol. 377, pp. 211-215.
International Search Report, issued Feb. 19, 2007 in International application No. PCT/EP2006/067950.
French Search Report, issued Oct. 5, 2006 in French application No. 0511113.

* cited by examiner

*Primary Examiner* — Michael G Hartley
*Assistant Examiner* — Sean R Donohue
(74) *Attorney, Agent, or Firm* — Foley & Lardner LLP

(57) ABSTRACT

The invention relates to using persistent luminescence nanoparticles, functionalised if necessary, in the form of an diagnosis agent for an in vivo optical imaging. Said nanoparticles are preferably consist of a compound selected from a group comprising (1) silicates, aluminates, aluminosilicates, germanates, titanates, oxysulphides, phosphates and vanadates, wherein said compounds contain at least one type of metal oxide, (2) the sulphides comprise at least one metal ion selected from zinc, strontium and calcium, and (3) metal oxides, wherein said compounds is doped with at least one rare earth ion, and possibly with at least one transition metal ion. In a preferred embodiment, the diagnosis agent is used for an organism vascularization imaging. A method and kit for detecting or quantifying in vitro a substance of biological or chemical interest in a sample by using said pre-functionalised nanoparticles are also disclosed.

12 Claims, 15 Drawing Sheets

PERSISTENT LUMINESCENCE NANOPARTICLES USED IN THE FORM OF A DIAGNOSIS AGENT FOR IN VIVO OPTICAL IMAGING

The invention relates to using persistent luminescence nanoparticles, functionalized if necessary, in the form of a diagnosis agent for in vivo optical imaging. Said nanoparticles preferentially consist of a compound selected from a group comprising (1) silicates, aluminates, aluminosilicates, germanates, titanates, oxysulfides, phosphates and vanadates, wherein said compounds contain at least one type of metal oxide, (2) the sulfides comprise at least one metal ion selected from zinc, strontium and calcium, and (3) metal oxides, wherein said compound is doped with at least one rare earth ion, and possibly with at least one transition metal ion. In a preferred embodiment, the diagnosis agent is used for body or reticulo-endothelial organ (liver, spleen) vascularization imaging. A method and kit for detection or quantifying, in vitro, a substance of biological or chemical interest in a sample by using said pre-functionalized nanoparticles are also disclosed.

The rapid development of numerous imaging techniques in recent decades (MRI, Doppler ultrasound, scanner, positron emission tomography, etc.) meets a growing need from biologists and medical doctors. From the simplification of experimental research to early disease detection, imaging tests have been the subject of dynamism. Each technique offers advantages and drawbacks, thus rendering all the different types of imaging complementary.

Optical imaging, using photons as an information source, is essentially used for in vitro studies. It represents a rapidly growing field with direct repercussions in pharmacology, in the development of diagnostic and research assistance tools for molecular and cellular biology.

Other imaging techniques mainly find their applications for in vivo imaging, whether in small animals or humans. An ever growing role is assigned to these techniques in biodistribution studies in biology. In fact, it is possible to perform dynamic and longitudinal monitoring on each animal, reducing animal sacrifices considerably. However, the high cost and number of technological barriers render their daily use difficult.

With the development of new more sensitive optical sensors (sensitivity of the order of one photon) and new high-performance probes, optical imaging is starting to focus on the problem of in vivo studies, with lower costs.

Optical imaging essentially uses fluorescent probes, whether they are organic molecular (rhodamine, ethidium bromide, etc.), biological (GFP type protein and similar) or inorganic (Quantum Dots) probes. However, the autofluorescence of tissues and all organic constituents, particularly in UV excitation, renders the use of fluorescence difficult. The problem is complicated further in the case of in vivo studies due to photon diffusion by tissues, which alters the shape and size of the zone observed. In fact, two well-known physical phenomena—absorption and diffusion—limit electromagnetic wave propagation in a medium, whether it is biological or not. In addition, light attenuation in tissues renders the observation of deep tissues difficult, if the probe emission property is not within the tissue transparency range (wavelength ranging from 650 nm to infrared). An illustration thereof is given in FIG. 1A (absorption spectrum of hemoglobin) and 1B (absorption spectrum of water). Between 400 and 600 nm, the absorption of all the constituents in the biological medium is very high for deep tissue imaging. Above 1300 nm, the electromagnetic waves are absorbed in the form of thermal energy by all molecules (particularly by water molecules).

Moreover, in numerous cases, fluorescent compounds are phototoxic. In fact, when a fluorophore (endogenous or exogenous) is excited, a triplet state may be created. This state is very chemically reactive and may damage living cells. One of the mechanisms inducing the most damage corresponds to singlet oxygen generation, giving rise to the oxidative stress chain.

In this way, all these factors limit the monitoring of molecules of interest in live animals significantly. For these reasons, the biodistribution of fluorescent compounds can only really be analyzed “ex vivo”, i.e. by sacrificing the animals to remove the organs, extract the fluorophore and evaluate the quantity with respect to the calibration corresponding to each organ. However, here again, significant difficulties arise due to the photo-deactivation of the organic chromophore after a few excitation cycles, which rapidly alters the fluorescence thereof.

In this way, although progress has been spectacular in terms of the technology of cameras and other detectors, considerable work still needs to be completed to develop probes that can be used in vivo for optical observation.

It is necessary to make a distinction between the various physical mechanisms whereby a molecule or a nanoparticle may emit light after excitation.

Luminescence is the generic term to characterize substances releasing in the form of photons of non-thermal origin a part of the energy absorbed during non-thermal excitation. The excitation of these compounds is carried out by supplying energy which may take several forms. It is possible to mention, without being exhaustive, excitation by wavelengths from the ultraviolet (UV), visible or infrared (IR) spectra, by means of X-rays, chemical reactions (chemoluminescence), enzyme reactions (bioluminescence), electrical excitations (electroluminescence) or mechanical excitations (triboluminescence).

Physical Phenomena Giving Rise to Luminescence:

It is appropriate to separate luminescence phenomena according to the nature of the substance emitting the photons, whether it is a molecule or a material.

For a molecule:

Luminescence is a deactivation of an excited molecule to a lower energy state. This phenomenon is conventionally differentiated into two types according to the time separating absorption and re-emission. If this time is short, the term fluorescence is used; if it is longer, the term phosphorescence is used.

The mechanism of fluorescence is as follows: the photons from a light source may be absorbed by the molecule, making it change from the fundamental state to an excited state. This light absorption takes place rapidly (approximately $10^{-15}$ s). Relaxation to the excited singlet state at a lower energy level, referred to as internal conversion, occurs by means of heat exchange with the medium in approximately $10^{-11}$ s. Subsequently, each molecule may lose its energy according to several processes. It may be de-excited either via radiation by emitting a photon, fluorescence which takes place in a time of the order of one nanosecond, or not via radiation by converting said energy into rotation or vibration energy.

However, another phenomenon may occur. It consists of the transfer of energy to a triplet excited state by means of inter-system crossing. For quantum reasons, the de-excitation from a triplet state to a singlet state (fundamental state) is impossible. Therefore, the electron remains blocked in this position for a relatively long time (from a few milliseconds to a few seconds), before changes to its environment enable radiative de-excitation. This is known as phosphorescence. It should be noted that, unlike fluorescence, the phosphorescence time is greatly affected by the temperature. In general, emission times are longer at low temperatures than at ambient temperature.

These different scenarios are summarized in the radiative diagram (FIG. 10). This diagram illustrates the various electron transitions and the various de-excitation phenomena.

Another slightly specific scenario exists. It is situated, in terms of emission time, between fluorescence and phosphorescence. It consists of long lived fluorescence. It is in fact possible from the $T_1$ state to return to the $S_1$ state. For this, the molecule must gain energy either by means of collision, or by means of absorption of another photon, or by means of transfer of energy between two $T_1$ states. In this case, the fluorescence observed appears later over time after absorption phenomena, while having the same emission spectrum as that observed with spontaneous fluorescence.

Another scenario involving long lived fluorescence is that of lanthanide chelates which may be described as follows: an organic chromophoric unit collecting the excitation energy is grafted onto a ligand complexing an inorganic lanthanide cation (generally europium, terbium or ruthenium). In some cases, the chelating agent serves directly as a chromophoric unit capturing the excitation. Due to the energy transfer time and rare earth-related quantum considerations, the emission time of these complexes may be up to several ms (FIG. 11).

For a material:

The types of materials that may be used as optical probes are, non-exhaustively:

- luminescent semiconductor nanocrystals ("quantum dots"),
- materials doped with rare earth ions or transition metals,
- silica or incorporating polymer nanoparticles or functionalized by the abovementioned radiative substances (organic radiative substances, lanthanide complexes, quantum dots).

Quantum Dots

Quantum dots (qdots) are inorganic nanocrystals of nanometric size. They consist of an inorganic semiconductor core (CdS, CdSe, ZnO, InP, InAs, etc.) responsible for light emission and are generally covered with an inorganic shell (ZnS) increasing the quantum yield and limiting photo-bleaching. The size of the inorganic crystal generally varies between 2 and 8 nm. It is finally necessary to functionalize them with organic molecules in order to graft biomolecules thereto and use them for biological applications.

The luminescence observed for qdots is due to the recombination of an electron-hole pair created during the light excitation in the semiconductor nanocrystal core. This recombination takes a relatively long time (approximately 20 to 30 ns) with respect to conventional radiation. However, the time is sufficiently short for the term fluorescence to be used to describe qdot luminescence.

Doped Materials

In order to give them optical properties, these materials are doped with absorbent and emitting ions, mainly lanthanide cations or transition ions. For materials doped with rare earth ions, the optical properties are very similar to those described above for lanthanide complexes with a luminescence time of the order of one ms. For materials doped with transition ions or other ions, the luminescence obtained is due to fluorescence emission from the dopants.

Silica or Incorporating Polymer Nanoparticles or Functionalized by the Abovementioned Fluorophores.

Polymer nanoparticles consist of an organic polymer matrix such as polystyrene, poly-methylmetacrylate (PMMA), dextrans, etc. The fluorophores may be trapped in the matrix during the synthesis thereof or subsequently by means of swelling of the polymer and diffusion of the fluorophores therein. Another method consists of directly polymerizing a monomer labeled with an organic fluorophore.

Silica nanoparticles are obtained by means of modified radiative synthesis. This synthesis consists of radiative hydrolysis in the presence of the radiative substance to be encapsulated in the silica matrix, by creating a micro-emulsion in the presence of a surfactant, in order to control the size of the particles obtained (the size may range from 20 nm to 1 μm) and the radiative substance concentration.

By means of functionalization methods, it is also possible to graft on this type of nanoparticles (as on all nanoparticles or material) all the fluorophores mentioned above.

Upconversion Phenomenon

Photon excitation at a specific wavelength (for example in the infrared spectrum) which is followed by luminescence at a shorter wavelength (for example in the visible spectrum) is referred to as "upconversion". It consists of a relatively unusual process as low-energy photons are "converted" into higher energy photons (FIG. 12). At least two IR photons are required to generate one photon in the visible spectrum. The upconversion phenomenon can only occur in materials for which multi-photon relaxation is not predominant, thus enabling the existence of more than one metastable excited state. In the case of rare earth, the electron-photon coupling of f-f transitions is reduced as the 4f or 5f electrons are not significantly involved in the metal-ligand bond. This results in a lower efficacy of multi-photon relaxation processes. In this way, the upconversion phenomenon is more common and, therefore, studied more in materials containing rare earths. However, there are transition metal systems and transition metal/rare earth combinations displaying this phenomenon. However, it is necessary to excite the material continuously for light emission to take place.

Persistent Luminescence Nanoparticles

The invention describes a new type of markers using persistent luminescence nanoparticles. The physical mechanism enabling photon emission several hours after the end of excitation is complex but may be described simply by means of the diagram in FIG. 13.

Excitation is generally carried out by means of light excitation in the UV or visible spectrum but may also be performed by means of X-rays. This excitation induces the formation of an exciton (i.e. electron-hole pair) which will separate (which is not possible in the case of quantum dots). Part of the energy captured will thus be "stored" in electron traps. Said trapped electron will then be released by means of thermal activation to be recombined on an emitter with emission of a photon.

In this way, the persistent luminescence material may be seen as a capacitor which charges under the effect of excitation and progressively discharges, emitting photons. Therefore, this mechanism is particularly different to all those mentioned above.

The inventors thus developed promising luminescent probes, that can be used both for in vivo imaging for small animals and in vitro imaging for the development of analysis tools for biologists.

The aim of the present invention is the use of persistent luminescence nanomaterials (materials wherein emission may persist for several hours after excitation has stopped) for in vivo optical imaging. The excitation of the material may thus be performed before said material is injected into the organism under study. This makes it possible to prevent tissue autofluorescence, an essential point for the increase in the signal-to-noise ratio.

For a given material, the emission wavelength depends on the dopant. Therefore, it is relatively modular and the emission may be adapted to the tissue transparency range, between 600 and 1300 nm. Persistent inorganic nanomaterials thus offer considerable advantages for the in vivo use thereof, firstly to improve image quality with deep tissue imaging and, secondly, in the form of nanometric particles, the material is rendered injectable, if applicable by means of surface treatment with biocompatible entities while retaining the optical qualities thereof.

Several applications are now envisaged: by means of these compounds, it is thus possible to view blood-brain barrier rupture zones, inflammatory and tumoral zones, and also view the biodistribution of liposomes in vivo in a gene therapy or medicinal product administration strategy using nanovectors.

As a document of the prior art, it is possible to cite the article by Jiang et al. (Journal of Alloys and Compounds 377 (2004) 211-215) which relates to the persistent luminescence property of $CaMgSi_2O_6$ doped with europium and dysprosium. However, this document does not describe nor suggests performing the excitation of this compound and administering same in vivo, particularly for optical imaging purposes. In fact, studies relating to persistent luminescence materials essentially relate to signaling, lighting, textile marking. No article noted in the literature relates to the subject of the present invention.

According to a first aspect, the present invention relates to a persistent luminescence nanoparticle for the use thereof as a diagnosis agent, said nanoparticle emitting photons at wavelengths between 400 and 1300 nm for at least 0.01 seconds, after light excitation at wavelengths between 100 and 800 nm, or after excitation by means of X-rays.

Wavelengths between 100 and 400 nm correspond to the ultraviolet/vacuum ultraviolet (VUV) spectrum, those between 400 and 800 nm to the visible spectrum, and those between 800 and 1300 correspond to the infrared spectrum.

The nanoparticles according to the invention should not emit photons at wavelengths below 400 nm, i.e. in the ultraviolet spectrum, as such wavelengths are absorbed by the molecules of the living being, which induce the progressive deterioration thereof, the formation of phototoxic compounds and finally cell destruction.

Moreover, the nanoparticles according to the invention should not emit photons at wavelengths above 1300 nm, i.e. in the far infrared spectrum, as the electromagnetic waves are absorbed in the form of heat energy by all molecules (particularly by water molecules).

The nanoparticles according to the invention emitting photons for less than 0.01 seconds are not included in the present application as this consists of fluorescence and no longer persistent luminescence.

Preferentially, the nanoparticle emits photons for at least 1 second, advantageously for at least 1 minute, 30 minutes, 1 hour, or at least 10 hours.

The persistence times are evaluated according to the luminescence intensity as a function of the time after excitation. Clear comparisons of persistence time measurements must be carried out under identical conditions using the same detection systems. The expression "persistent luminescence material" was applied to materials displaying a luminescence from at least 0.01 seconds to several hours. Persistent luminescence materials, including simple crystals and simple crystal fibers, may display luminescence persistence times greater than approximately 3 to 5 hours, greater than approximately 10 to 12 hours, or greater than approximately 15 to 18 hours.

The persistent luminescence phenomenon involves two types of active centers: emitters and traps (sensors). Emitters are centers capable of emitting radiation after excitation of the center. Traps do not emit radiation, but store the radiation energy and release it progressively to the emitter. Emitter centers may be created by adding activators, i.e. small quantities of impurity atoms or ions added intentionally to the host matrix. Co-activators are impurity ions or isolated defects (anion holes) added intentionally which may affect (improve or modify) the emission lifetime of the first activator. For example, a co-activator may be added to form capture centers liable to improve the persistence time of the persistent luminescence material.

It is possible for an ion to transfer energy to another. If two different ions are involved in the transfer energy, the ion transferring the energy is referred to as a donor while the ion receiving the energy is referred to as the acceptor or activator (G. Blasse and B. C. Grabmaier, 1994, "Luminescent materials", Springer-Verlag, Berlin, p. 91).

The materials according to the present invention are based on the doping of one or more emitters in a host matrix. The host (or matrix) and the emitter ion(s) are selected to supply the desired emission or the persistent luminescence color and a high quantum yield.

The present invention is applicable to any type of species from the animal kingdom, advantageously to vertebrates and more specifically to small animals (rodents), but also to humans.

In the present application, the term "nanoparticle" is used to refer to a particle wherein the size, defined as the greatest dimension along an axis, is generally between 10 nm and 10 μm.

Preferentially, the nanoparticle according to the invention is between 25 nm and 1 μm, even more preferentially, between 50 nm and 500 nm.

The persistent luminescence nanoparticle may thus consist as a non-limitative example of a compound such as $CdSiO_3$:$Mn^{2+}$, $ZnGa_2O_4$:$Mn^{2+}$, ZnS:Cu or $Y_2O_2S$:Ti, Mg, Ca. It may consist of a compound of the silicate, aluminate, aluminosilicate, germanate, titanate, oxysulfide, phosphate or vanadate type, said compound comprising at least one metal oxide and being doped with at least one rare earth ion, and possibly with at least one transition metal ion (for example manganese or trivalent chromium). It may also consist of a sulfide comprising at least one metal ion selected from zinc, strontium and calcium, doped with at least one rare earth ion, and possibly with at least one transition metal ion. Examples also include metal oxides, again doped with at least one rare earth ion and possibly with at least one transition metal ion.

This list of compounds is non-limitative and those skilled in the art are able to determine which persistent luminescence materials may be used within the scope of the present invention.

Preferentially, the nanoparticle consists of a compound selected from the group consisting of:

- silicates, aluminates, aluminosilicates, germanates, titanates, oxysulfides, phosphates and vanadates, such compounds comprising at least one metal oxide,
- sulfides comprising at least one metal ion selected from zinc, strontium and calcium, and
- metal oxides, said compound being doped with at least one rare earth ion, and possibly with at least one transition metal ion.

Examples of oxysulfides include yttrium-based compounds such as yttrium oxide sulfides ($Y_2O_2S$, etc.). The germanates include $MGeO_3$ wherein M is magnesium, calcium or zinc, preferentially magnesium ($Mg^{2+}$) and calcium ($Ca^{2+}$), such germanates being preferentially doped with manganese ions and a trivalent ion from the lanthanide series. Examples of titanates include MO—$TiO_2$ wherein M is magnesium or zinc, and the sulfides include zinc sulfide (ZnS), calcium sulfide (CaS) and strontium sulfide (SrS).

The metal of the metal oxide may be of any type. Preferentially, it is selected from magnesium, calcium, strontium, barium, zinc, cadmium, yttrium and gallium.

The transition metal may be of any type. Preferentially, the transition metal is selected from manganese, chromium and titanium ($Mn^{2+}$, $Cr^{3+}$, $Ti^{4+}$, etc.).

The rare earth ion may be of any type. Preferentially, the rare earth ion is selected from europium, ytterbium, cerium, samarium, praseodymium, dysprosium, neodymium, holmium, terbium, thulium and erbium ions. The rare earth ion is found in the trivalent form thereof ($Ce^{3+}$, $Dy^{3+}$, $Nd^{3+}$, $Ho^{3+}$, $Er^{3+}$, etc.) except for europium, samarium and ytterbium, which may also be found in the divalent form thereof ($Eu^{2+}$, $Sm^{2+}$ and $Yb^{2+}$).

Preferentially, the nanoparticle consists of a silicate comprising a metal oxide doped with at least one rare earth ion and at least one transition metal ion. More preferentially, the silicate is doped with manganese, europium and dysprosium ions.

More preferentially, the nanoparticle consists of a compound selected from the group consisting of the silicates $ZnMgSi_2O_6$, $CaMgSi_2O_6$ and $MgSiO_3$, such silicates being doped with manganese, europium and dysprosium ions, and $Sr_2MgSi_2O_7$ doped with europium and dysprosium ions.

According to another particularly preferential embodiment, the nanoparticle consists of the silicate $Ca_{0.2}Zn_{0.9}Mg_{0.9}Si_2O_6$ doped with $Eu^{2+}$, $Dy^{3+}$, $Mn^{2+}$.

As a general rule, the nanoparticles according to the invention may be administered without being functionalized in the body or tissue. In particular, when injected by the intra-arterial or intravenous route, they enable imaging of the vascular system, particularly in the lungs and liver. They also enable functional imaging of the liver. One of the aims is imaging of tumoral or inflammatory zones which are hypervascularized. In the case of tumoral zones, early detection of cancer such as breast cancer is possible.

According to a particular embodiment, the nanoparticle according to the invention is functionalized by coating and/or grafting a ligand enabling bonding with a substance of biological or chemical interest.

The term substance of biological or chemical interest refers to any substance wherein it is intended to determine the biodistribution in a body or in a tissue. The substance of interest may be for example a chemical molecule such as an active ingredient or a toxic substance. It may also consist of an extracellular receptor, a hormone, an antibody or an antigen, a protein, a toxin such as bacterial toxin possibly in the attenuated form thereof or a nucleic acid, a virus or other pathogenic agent (bacterium, etc.).

The terms protein, polypeptide or peptide refer indifferently to an amino acid sequence or, for the derivatives thereof, a compound containing an amino acid sequence. Similarly, the terms nucleic acid, nucleic or nucleic acid sequence, polynucleotide, oligonucleotide, polynucleotide sequence, nucleotide sequence, are used indifferently to refer to a specific sequence of nucleotides, modified or not, making it possible to define a fragment or a region of a nucleic acid, comprising non-natural nucleotides or not, and possibly corresponding equally well to double-strand DNA, single-strand DNA and transcription products of said DNA. Said nucleic acids are isolated from their natural environment and are natural or artificial.

In order to determine the biodistribution of a substance of biological or chemical interest in a body or in a tissue, it is necessary to functionalize the nanoparticle by coating and/or grafting a ligand capable of binding with the substance, if applicable present in the tissue of the organ of interest.

The coating methods are well known to those skilled in the art. For example, the coating may be performed by bonding with molecules carrying phosphate, carboxylate or thiol groups, or by means of the heteroprecipitation of silica, aminosilane, or preferentially triethoxyaminopropylsilane. Coating performed with triethoxyaminopropylsilane offers the advantage that a single layer is formed, with no polymerization toward the outside inducing an increase in the size of the nanoparticles.

Similarly, the ligand grafting (or coupling) methods are well known to those skilled in the art. It generally consists of coupling by means of a covalent bond, affinity, passive or forced adsorption. In the case of coupling by means of a covalent bond, the nanoparticles carry chemical groups capable of reacting with another chemical group carried by the ligand to form a covalent bond.

As examples of chemical groups liable to be present on the surface of the nanoparticles, it is possible to cite, but without being limited thereto, carboxyl, amino, aldehyde and epoxy groups.

It is also possible to use interaction by means of affinity, which is generally applied by two partners of a high-affinity bonding pair such as in particular, but without being limited thereto, (poly) carbohydrate/lectin pairs, biotin or biotinilated/avidine or streptavidine compounds, receptor/specific ligand or haptene/antibody, etc.

The grafting of the coated nanoparticles may also be carried out either directly or using spacer arms also referred to using the terms "linker" or "spacer".

Passive or forced adsorption coupling is known to those skilled in the art. It is possible to use for example BSA-biotin (Bovine Serum Albumin) (Sigma, Lyon, FR-Ref. A-8549).

Preferentially, the coating is performed by means of precipitation on the surface of triethoxyaminopropylsilane.

According to another preferential embodiment, polyethylene glycol (PEG) is grafted for stealth purposes (to obtain a greater circulation time in the body). It is generally carried out as follows: the PEG is firstly coupled with the ligand, and the coupling product is grafted onto the nanoparticle.

Even more preferentially, the nanoparticle according to the invention is functionalized by means of precipitation on the surface of triethyoxyaminopropylsilane and then grafting of methoxy-$PEG_{5000}$-COOH enabling bonding with the substance of biological or chemical interest.

In addition, toluene may be replaced by dimethylformamide, thus enabling improved particle dispersion. The particles may be functionalized by carboxylate groups (by means of a diglycol anhydride reaction on the aminated particles) but also thiol groups by means of a direct reaction with 3-mercaptopropyl-triethoxysilane. Grafting of polyethylene glycol (PEG) may be performed directly by means of peptide coupling (see Example 5). The inventors also succeeded in grafting different chemical molecules on the surface of the nanoparticles (biotin, peptide).

According to a preferred embodiment, the nanoparticle according to the invention is functionalized by carboxylate, thiol or free amine groups.

According to a specific embodiment, the present invention relates to a nanoparticle as defined above for the use thereof as a diagnosis agent intended for in vivo optical imaging.

Preferentially, said nanoparticle is excited before administration. Indeed, the absence of optical excitation of the subject makes it possible to eliminate tissue autofluorescence, an essential point for the increase in the signal-to-noise ratio.

Preferentially, the diagnosis agent is administered in a body under study by injection by the intravenous, intra-arterial or intramuscular route.

Preferentially, the diagnosis agent is intended for imaging of the vascularization of the body or reticulo-endothelial organs (liver, spleen).

As a general rule, it is preferential to use nanoparticles emitting photons at wavelengths between 600 and 1300 nm (see FIG. 1) for deep tissue imaging (organs, etc.).

Vascular imaging is, for example, of interest for detecting angiogenic processes in chronic inflammation, tumoral growth or metastasis localization. Moreover, biodistribution studies are essential to determine the accumulation ratios of an agent vectorized or not by specific forms in the target tissues.

More preferentially, the diagnosis agent is intended for the imaging of tumoral, inflammatory or retinal zones, said zones being liable to be hypervascularized, or blood-brain barrier rupture zones.

According to another embodiment, the diagnosis agent is intended for the imaging of hypovascularized zones such as in the case of cerebral or cardiac ischemia, or in the case of cranial trauma.

According to another embodiment, the diagnosis agent makes it possible to mimic the biodistribution of liposomes or nanovectors in vivo in a gene therapy strategy.

According to a second aspect, the present invention relates to a method for the in vitro detection or quantification of a substance of biological or chemical interest in a sample, which comprises the following steps:

1) placing in contact of said sample with a solution containing persistent luminescence nanoparticles previously functionalized so as to form a complex between the substance and the nanoparticles, and 2) the detection or quantification of said complex formed, characterized in that said nanoparticles consist of a compound selected from the group consisting of:

- silicates, aluminosilicates, germanates, titanates, oxysulfides, phosphates and vanadates, such compounds comprising at least one metal oxide,
- sulfides comprising at least one metal ion selected from zinc, strontium and calcium, and
- metal oxides, said compound being doped with at least one rare earth ion, and possibly with at least one transition metal.

The term sample in the method according to the present invention refers to any sample liable to contain the substance of biological or chemical interest to be detected or quantified.

Examples of oxysulfides include yttrium-based compounds such as yttrium oxide sulfides ($Y_2O_2S$, etc.). The germanates include MO—$GeO_2$ wherein M is magnesium, calcium or zinc, the titanates include MO—$TiO_2$ wherein M is magnesium or zinc, and the sulfides include zinc sulfide (ZnS), calcium sulfide (CaS) and strontium sulfide (SrS).

Preferentially, the metal of the metal oxide is selected from magnesium, calcium, strontium, barium, zinc, cadmium, yttrium and gallium.

Preferentially, the transition metal is selected from manganese, chromium and titanium ($Mn^{2+}$, $Cr^{3+}$, $Ti^{4+}$, etc.).

Preferentially, the rare earth ion is selected from europium, ytterbium, cerium, samarium, praseodymium, dysprosium, neodymium, holmium, terbium, thulium and erbium ions. The rare earth ion is found in the trivalent form thereof ($Ce^{3+}$, $Dy^{3+}$, $Nd^{3+}$, $Ho^{3+}$, $Er^{3+}$, etc.) except for europium, samarium and ytterbium, which may also be found in the divalent form thereof ($Eu^{2+}$, $Sm^{2+}$ and $Yb^{2+}$).

More preferentially, the nanoparticles consist of a silicate comprising a metal oxide doped with at least one rare earth ion and at least one transition metal ion.

Most preferentially, the nanoparticles consist of a compound selected from the group consisting of the silicates $ZnMgSi_2O_6$, $CaMgSi_2O_6$ and $MgSiO_3$, such silicates being doped with manganese, europium and dysprosium ions, and $Sr_2MgSi_2O_7$ doped with europium and dysprosium ions.

According to a particularly preferential embodiment, the method according to the present invention for the in vitro detection or quantification is characterized in that the nanoparticles consist of the silicate $Ca_{0.2}Zn_{0.9}Mg_{0.9}Si_2O_6$ doped with $Eu^{2+}$, $Dy^{3+}$, $Mn^{2+}$.

The nanoparticles may be functionalized as described above.

According to a final aspect, the invention relates to a diagnosis kit comprising a solution containing persistent luminescence nanoparticles consisting of a compound selected from the groups consisting of:

- silicates, aluminates, germanates, titanates, oxysulfides, phosphates and vanadates, such compounds comprising at least one metal oxide,
- sulfides comprising at least one metal ion selected from zinc, strontium and calcium, and
- metal oxides, said compound being doped with at least one rare earth ion, and possibly with at least one transition metal.

Preferentially, the kit is characterized in that the nanoparticles consist of a silicate comprising a metal oxide doped with at least one rare earth ion and at least one transition metal. More preferentially, the kit is characterized in that the nanoparticles consist of a compound selected from the group consisting of the silicates $ZnMgSi_2O_6$, $CaMgSi_2O_6$ and $MgSiO_3$, such silicates being doped with manganese, europium and dysprosium ions, and $Sr_2MgSi_2O_7$ doped with europium and dysprosium ions. According to another preferential embodiment, the kit is characterized in that the nanoparticles consist of the silicate $Ca_{0.2}Zn_{0.9}Mg_{0.9}Si_2O_6$ doped with $Eu^{2+}$, $Dy^{3+}$, $Mn^{2+}$.

The examples and figures below are intended to illustrate the invention without in any way limiting the scope thereof.

(14A) X-ray diffraction diagram (Intensity a.u. on Y-axis).

(14B) Images obtained by means of transmission electron microscopy (scale: 200 nm)

(14C) Excitation spectrum (Standardized spectrum on Y-axis)

(14D) Persistent luminescence emission spectrum (Standardized Intensity on Y-Axis)

(14E) Decline of luminescence of compound (Intensity a.u. on Y-axis).

Figure 15:
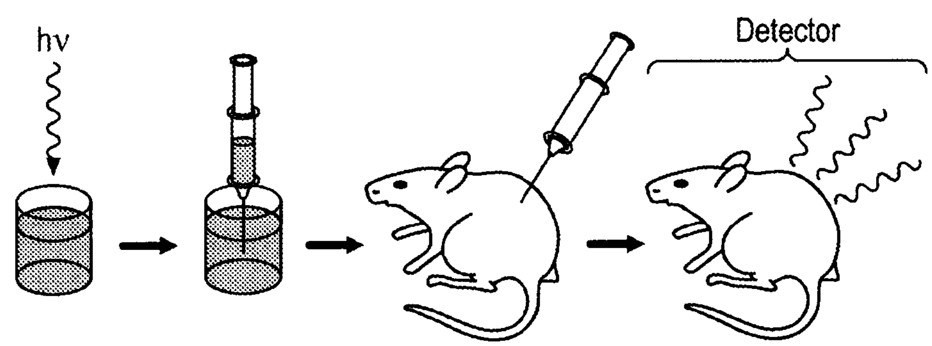

FIG. 15: Principles of in vivo experiments using the persistent luminescence properties of the synthesized nanoparticles FIG. 16: Possible functionalization diagram to obtain particles carrying different surface loads (i) APTES (ii) diglycol anhydride (iii) mPEG-COOH, BOP, $Et_3N$ FIG. 17: Intensity of signal obtained following a system injection of persistent luminescence nanoparticles in two types of mice (Swiss mice and C57B1/6 mice)

Figure 18:
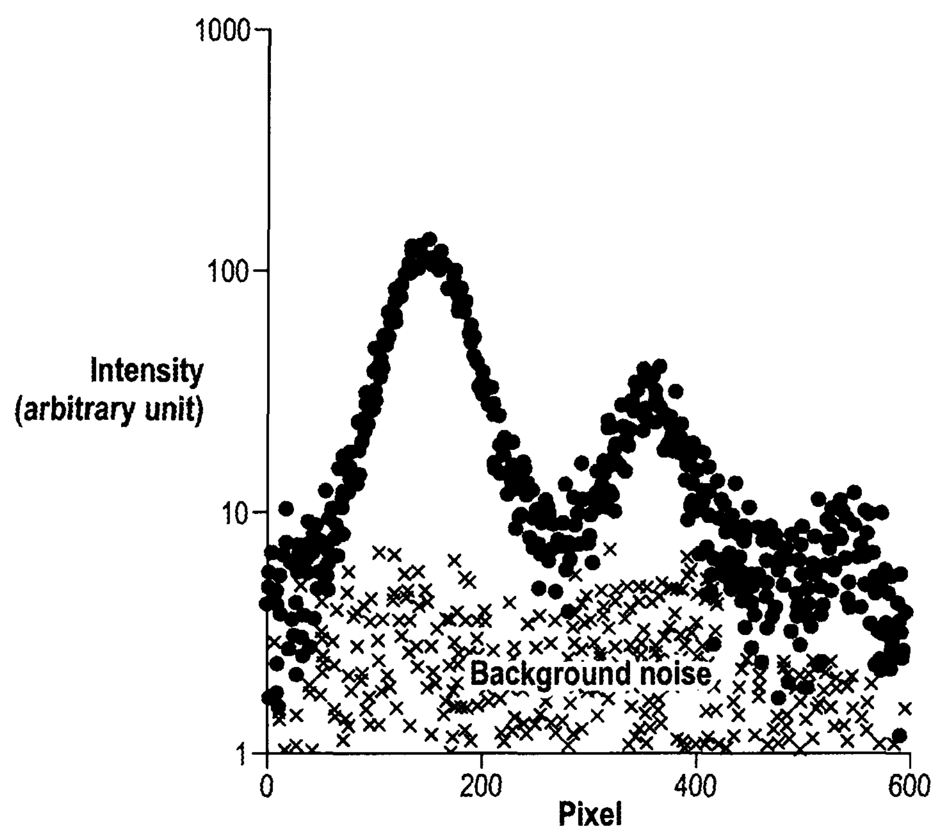
Figure 18:
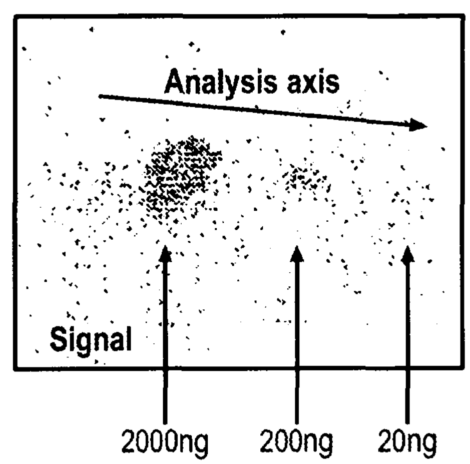

FIG. 18: Analysis of signal obtained following three subcutaneous injections of nanoparticles (2 µg, 200 ng and 20 ng) on the back of a mouse.

Image of signal obtained demonstrating the analytical axis selected, the location and quantity of nanoparticles injected.

Figure 19:
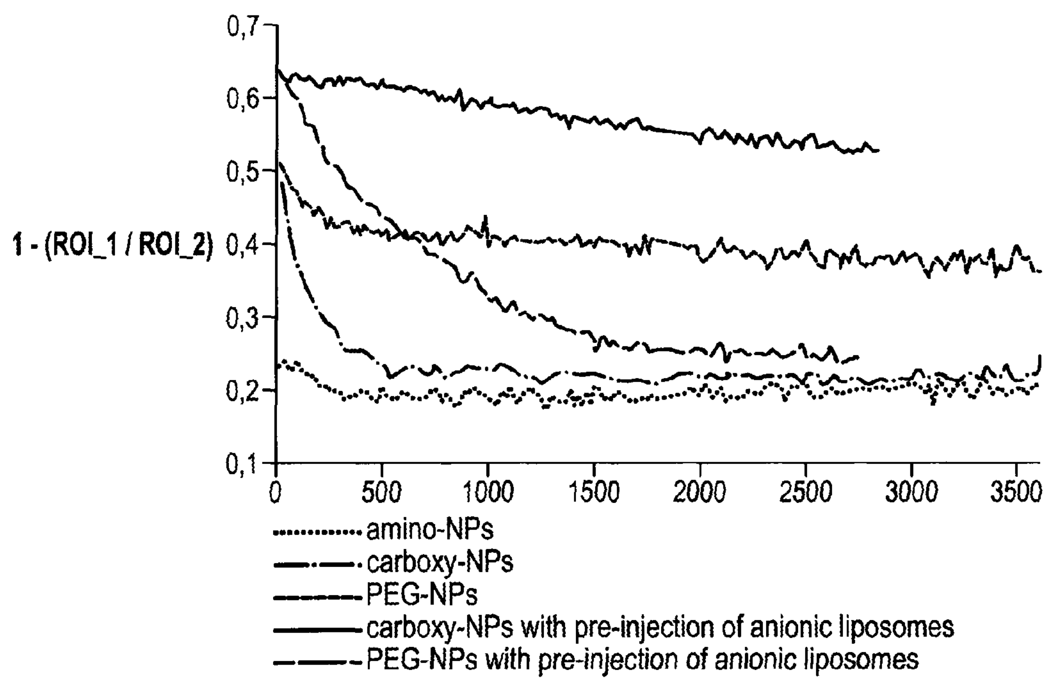

FIG. 19: Analysis of the light intensity distribution according to the type of nanoparticles injected (amino-NPs, carboxy-NPs and PEG-NPs) with or without pre-injection of an anionic liposome suspension. ROI_1 corresponds to the signal from the region of interest covering the lungs, liver and spleen. ROI_2 corresponds to the signal from the region of interest covering the entire mouse.

Figure 20:
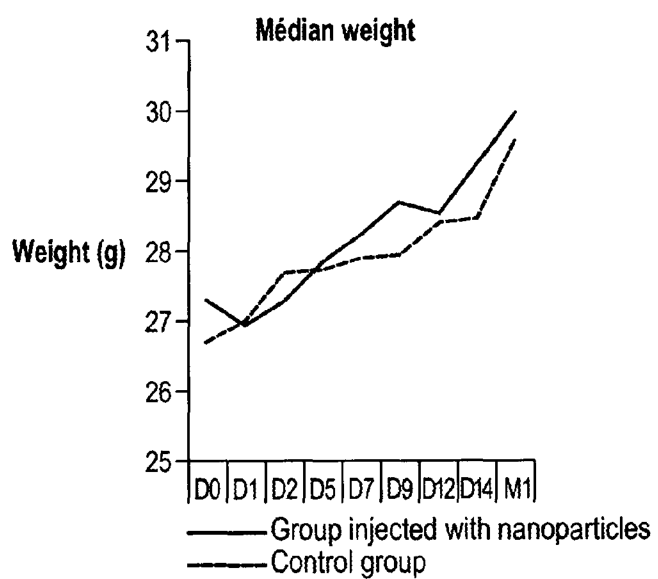

FIG. 20: Median weight of the group of mice injected with 1 mg of nanoparticles and the control group (injected with physiological saline solution).

Figure 21:
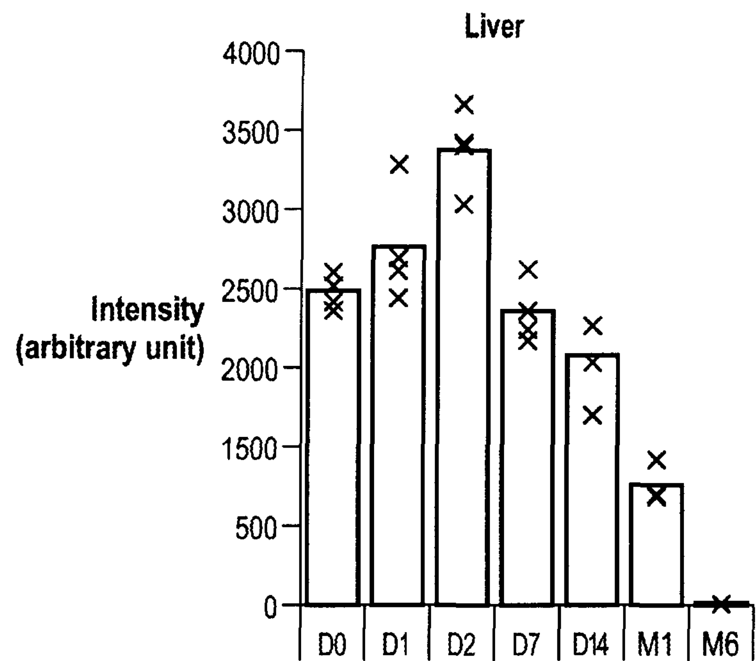

FIG. 21: Quantity of nanoparticles detected over time in the liver (analysis conducted on a group of 4 mice for each time).

Figure 22:
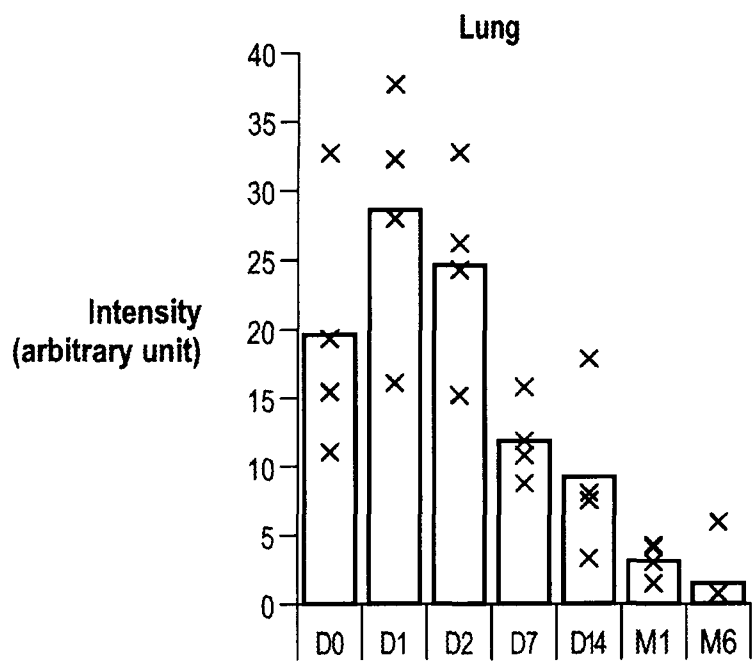

FIG. 22: Quantity of nanoparticles detected over time in the lungs (analysis conducted on a group of 4 mice for each time).

Figure 23:
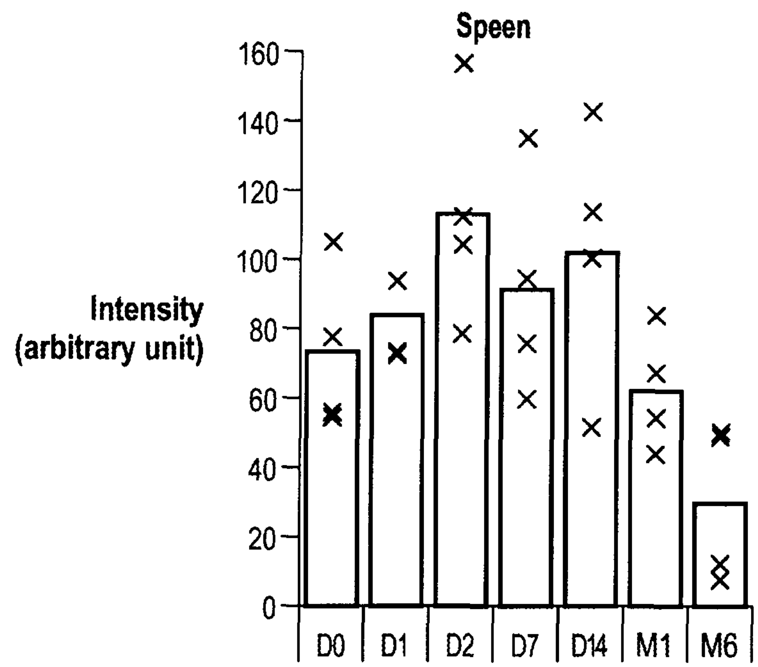

FIG. 23: Quantity of nanoparticles detected over time in the spleen (analysis conducted on a group of 4 mice for each time).

Figure 24:
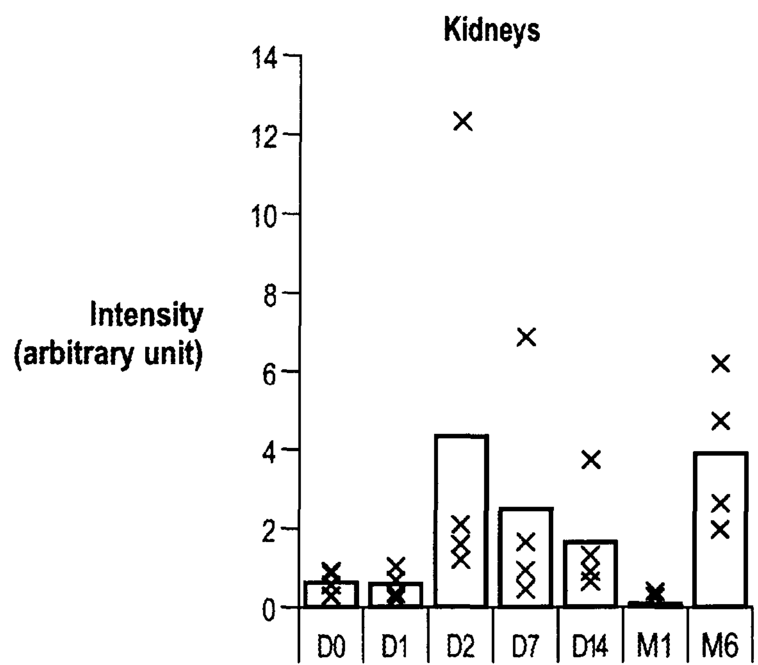

FIG. 24: Quantity of nanoparticles detected over time in the kidneys (analysis conducted on a group of 4 mice for each time).

EXAMPLES

Example 1

Gel Synthesis of Compound $ZnMgSi_2O_6$ Doped with Eu, Mn, Dy

1) Gel Synthesis

In a flask, 610 mg ($4.98.10^{-3}$ mol) of Zinc Chloride, 1.150 mg ($4.98.10^{-3}$ mol) of Magnesium Nitrate hexahydrate, 20 mg ($4.98.10^{-3}$ mol) of Europium Nitrate hexahydrate, 58.6 mg ($1.49.10^{-4}$ mol) of Dysprosium Nitrate hexahydrate and 29.4 mg ($1.34.10^{-4}$ mol) of Manganese Chloride tetrahydrate are dissolved in 4 ml of acidified water at pH 2 (by adding nitric acid).

Under stirring, 2 ml ($8.96.10^{-3}$ mol) of tetraethoxysilane is added. The whole is stirred vigorously using a vortex to homogenize the solution and is left under stirring at ambient temperature for 3 hours.

2) Drying

When the solution is completely single-phased (after approximately three hours of stirring), the flask is placed in an oven at 60° C. for four hours. A translucent gel is then obtained. The samples are then oven-dried at 110° C. for 12 hours.

3) Heating

The materials are then heated in a furnace in a reducing atmosphere (Noxal is used: 90% Ar, 10% $H_2$). The heating is performed in three steps, the temperature rise: 20° C./min up to 1150° C., a plateau for 10 hrs (constant 1150°) followed by a decline in temperature by 10° C./min to ambient temperature.

After this first heating, heating in air followed by heating in a reducing atmosphere may be necessary to improve the luminescence.

The gel synthesis of the compounds $CaMgSi_2O_6$ doped with Eu, Mn, Dy, $MgSiO_3$ doped with Eu, Mn, Dy, and $Sr_2MgSi_2O_7$ doped with Eu, Dy is performed in a similar way.

Example 2

Physical Properties of Exemplified Compounds

Figure 1A:
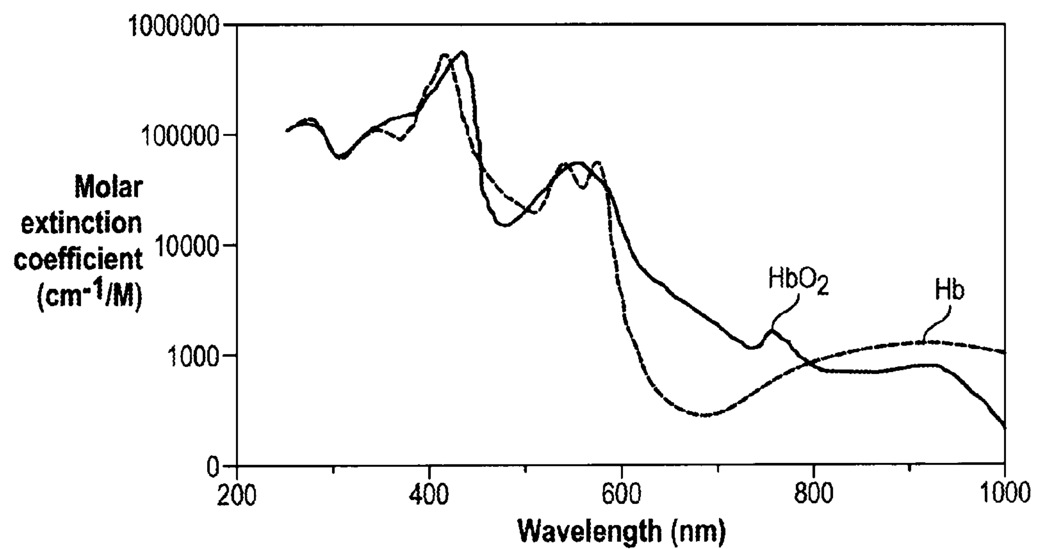
FIG. 1: 1A Molar extinction coefficient of hemoglobin as a function of wavelengths (as per W. B. Gratzer and N. Kollias); 1B Extinction coefficient of water as a function of wavelengths (as per G. M. Hale, M. R. Querry. Applied Optics, 12 (1973) 555-563)
Figure 1B:
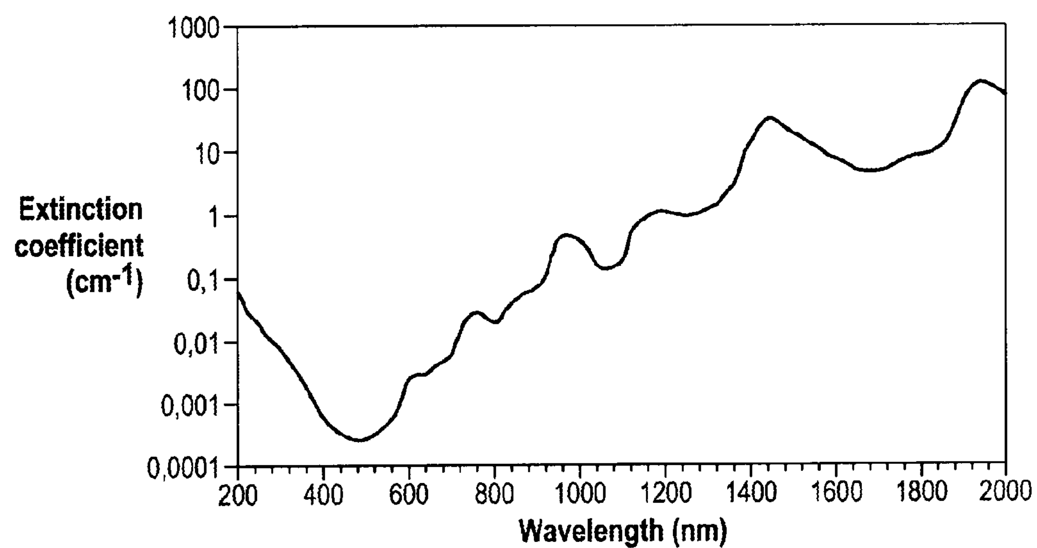
Figure 2:
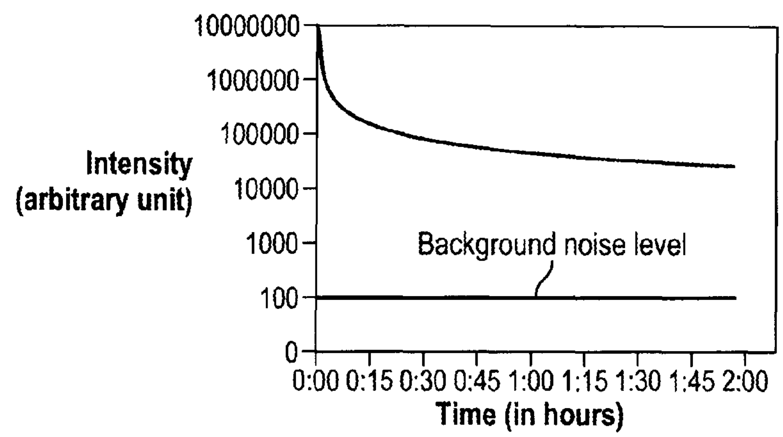
FIG. 2: Typical decline of luminescence signal of the synthesized compounds

The compounds $ZnMgSi_2O_6$, $CaMgSi_2O_6$, $MgSiO_3$ doped with Eu, Mn, Dy and $Sr_2MgSi_2O_7$ doped with Eu, Dy obtained by means of sol-gel synthesis as detailed above (example 1), have a persistent luminescence of several hours (more than two hours, see FIG. 2). However, these relative compositions may be modified to improve the luminescence properties of compounds. By means of the sol-gel synthesis described above, the compounds retain a mesoscopic size (size between 10 nm and 1 µm, preferentially between 50 and 500 nm). It is thus possible to redisperse same in an aqueous solution to obtain an injectable luminescent solution.

Figure 3:
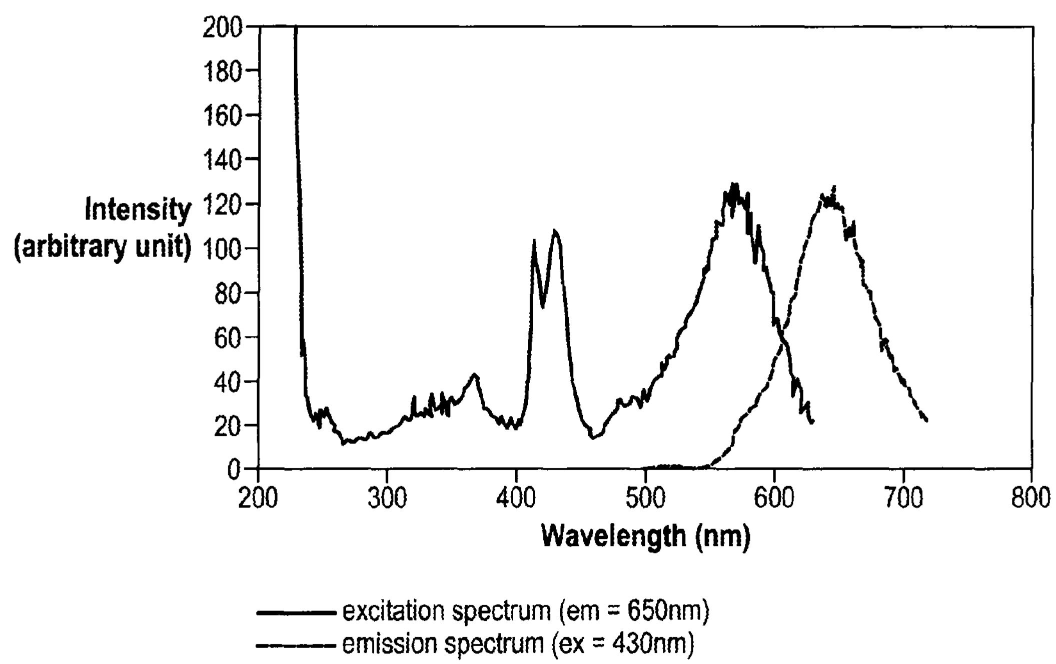
FIG. 3: Excitation and emission spectrum of $ZnMgSi_2O_6$:$Eu^{2+}$ $Dy^{3+}$ $Mn^{2+}$
Figure 4:
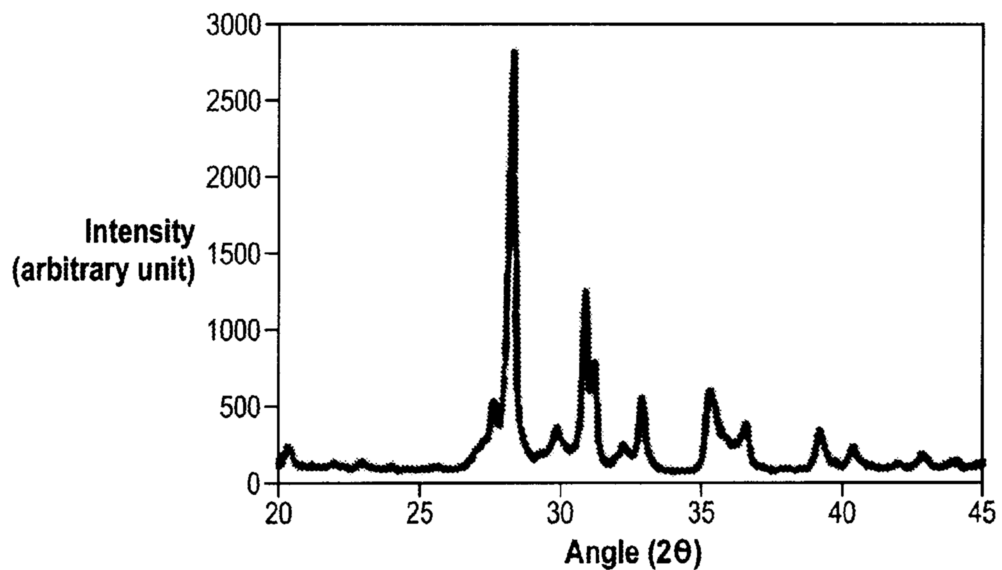
FIG. 4: X-ray diffraction diagram of $ZnMgSi_2O_6$:$Eu^{2+}$ $Dy^{3+}$$Mn^{2+}$
Figure 5:
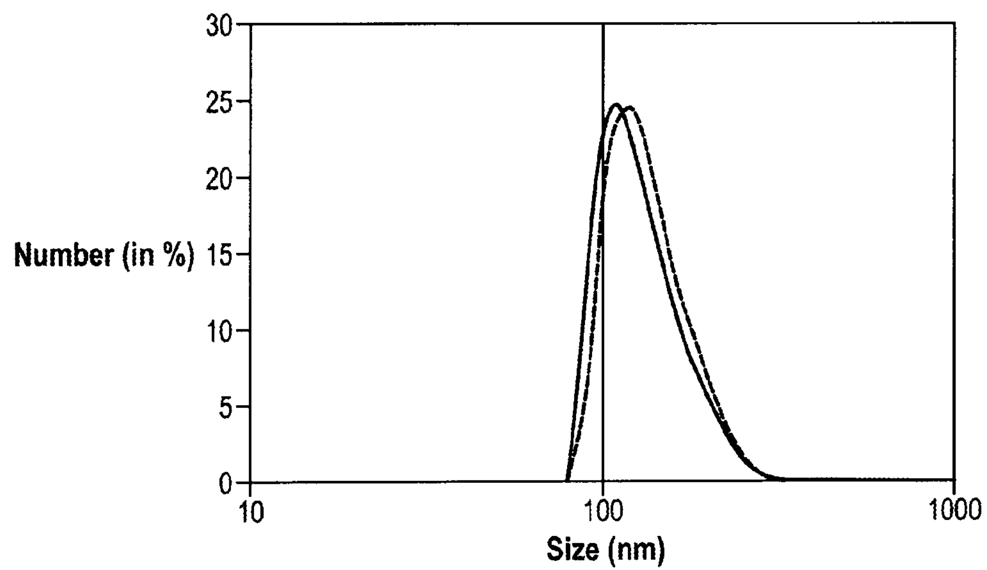
FIG. 5: Size distribution obtained by means of quasi-elastic diffusion of light from particles of $ZnMgSi_2O_6$:$Eu^{2+}Dy^{3+}Mn^{2+}$
Figure 6:
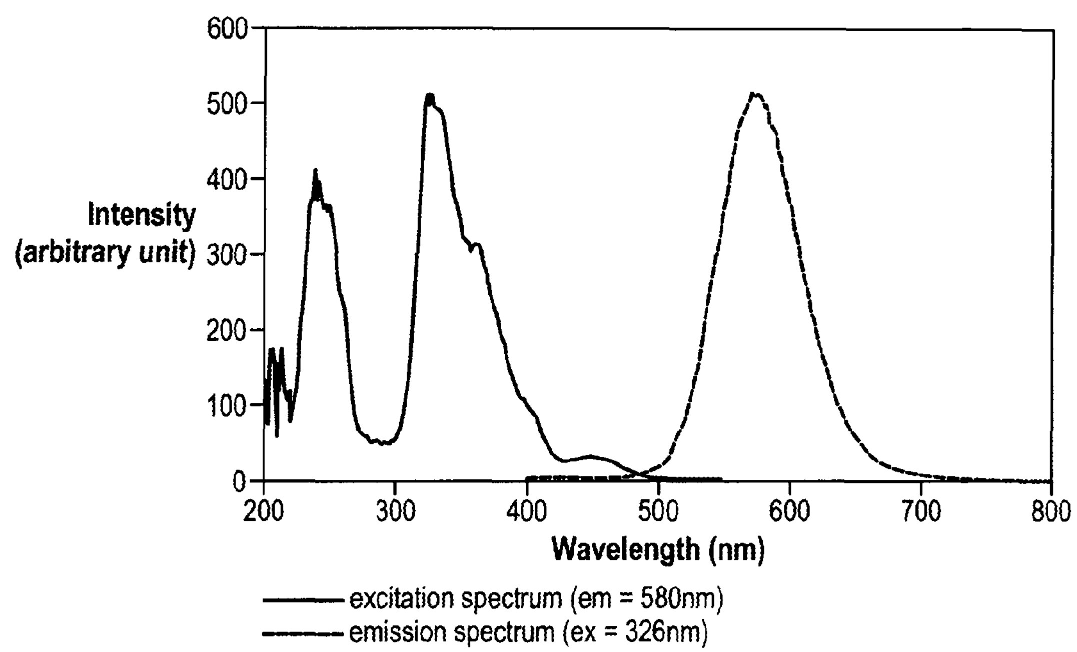
FIG. 6: Excitation and emission spectrum of $CaMgSi_2O_6$:$Eu^{2+}Dy^{3+}Mn^{2+}$
Figure 7:
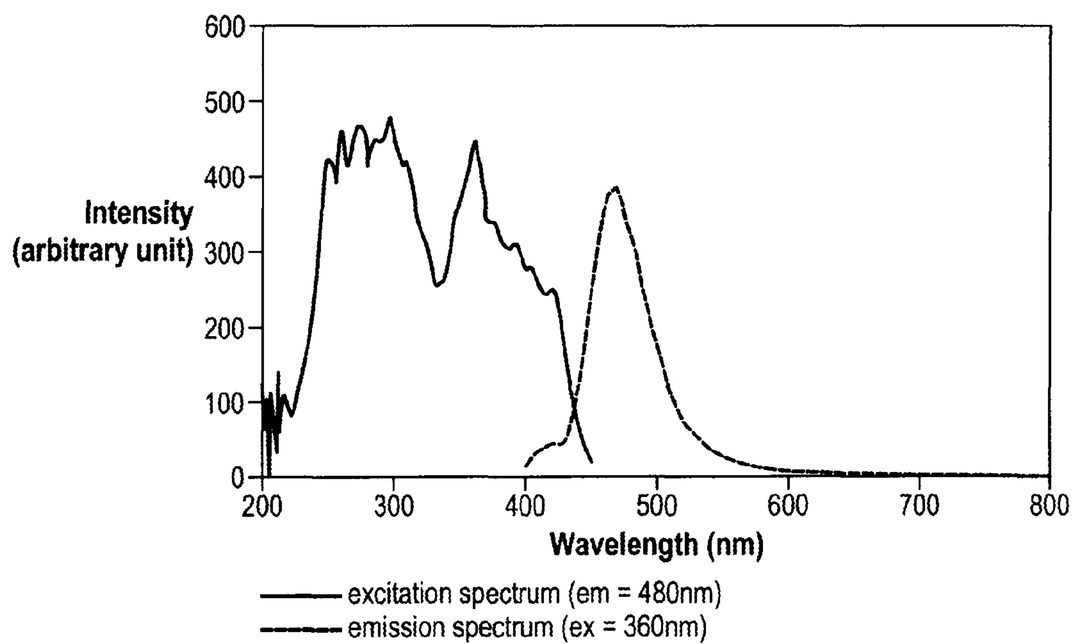
FIG. 7: Excitation and emission spectrum of $Sr_2MgSi_2O_7$:$Eu^{2+}Dy^{3+}$

Some exemplified compounds have a persistent luminescence at wavelengths of particular interest for biological media (see FIG. 3). The persistent luminescence mechanism with a transfer of excitation to manganese emits around 650 nm in these matrices. By means of this long emission in the red spectrum, it is thus possible to perform in vivo optical imaging, the transparency zone of the biological tissues being between 600 and 1300 nm.

Example 3

Precipitation of Triethoxyaminopropylsilane Followed by Grafting of Methoxy-$PEG_{5000}$-COOH on the Surface of Persistent Luminescence Nanoparticles Surface Pre-Treatment:

In a flask containing an aqueous sodium hydroxide (5 mM) solution, 75 mg of nanoparticles are dispersed. The suspension is stirred at ambient temperature for 3 hours. Following the addition of hydrochloric acid (1M) in order to return to neutral pH, the suspension is then centrifuged (4500 rpm, 10 min) to remove the supernatant. The powder retrieved from the oven is then dried.

Precipitation of Triethoxyaminopropylsilane:

In a flask containing 5 ml of anhydrous toluene and 90 μl of triethoxyaminopropylsilane, 75 mg of previously treated nanoparticles are dispersed. The whole is left under stirring for 4 hours at 80° C. The suspension is then centrifuged (4500 rpm, 10 min) to remove the supernatant. To wash the solution, the powder is then redispersed in 5 ml of anhydrous toluene and centrifuged. This washing operation is thus repeated three times. The powder is finally oven-dried.

A primary amine characteristic test with 2,4,6 trinitrobenzene sulfonic acid proves to be positive on the nanoparticles.

Grafting of activated methoxy-PEG-COOH onto the nanoparticles:

In a flask containing 5 ml of dichloromethane, 250 mg ($5.10^{-4}$ mol) of methoxy-$PEG_{5000}$ COOH is dissolved. 5.8 mg of N-hydroxysuccinimide ($5.10^{-4}$ mol) and 10.3 mg of dicyclohexylcarbodiimide ($5.10^{-5}$ mol) are added. The whole is left under stirring at ambient temperature for 2 hours.

The solvent is then evaporated and the activated polymer is precipitated in diethyl ether. The precipitate formed in this way is washed with ether and then redissolved in 5 ml of dichloromethane.

In the solution 15 μl of triethylamine and 50 ml of nanoparticles coated with a layer of aminosilane are added. The reaction medium is left under stirring for 3 hours.

The solvent is then evaporated and the nanoparticles are redispersed in water. After centrifugation (4500 rpm, 10 min) and washing with water, the PEGylated nanoparticles dried in the oven are retrieved.

Example 4

Experiments Conducted

In view of the first physical results of the synthesized powder, the inventors conducted the first in vitro (sampling of organs and observation on sections) and in vivo experiments with these persistent luminescence compounds. The in vivo injections were conducted on a SWISS mouse with a luminescent material solution at a concentration of 30 mg per ml. The in vivo experiments were conducted in accordance with the principles of good laboratory practices.

The excitation of the solution is performed before injection by means of irradiation under a non-filtered conventional UV lamp. The powders did not undergo any specific functionalization (basic grinding in acid medium (HCl) to obtain surface loads rendering the nanoparticles redispersable in aqueous medium). It should be noted that the compounds remain luminescent in biological media (which is not the case for all persistent luminescence materials. For these other compounds, it is necessary to coat the nanoparticles). The images were produced using the Biospace Mesures PhotoImager camera.

Following intramuscular injection, the results demonstrate that the exemplified materials, previously irradiated under a UV lamp, are still luminescent following injection into the animal. The luminescence is sufficiently significant to pass through several millimeters of tissues conventionally studied in biology. The strong localization of the signal is in line with expectations, the particles injected by the intramuscular route not being normally carried by the blood circulation.

The intravenous injections were made on the tail of the mouse. The particles are thus immediately carried by the blood circulation. The particles being of nanometric size, they are not blocked in the lungs and are therefore naturally found in the liver.

The signal is sufficient to obtain in vivo optical imaging of the particles for more than thirty minutes after the injection.

Figure 8:
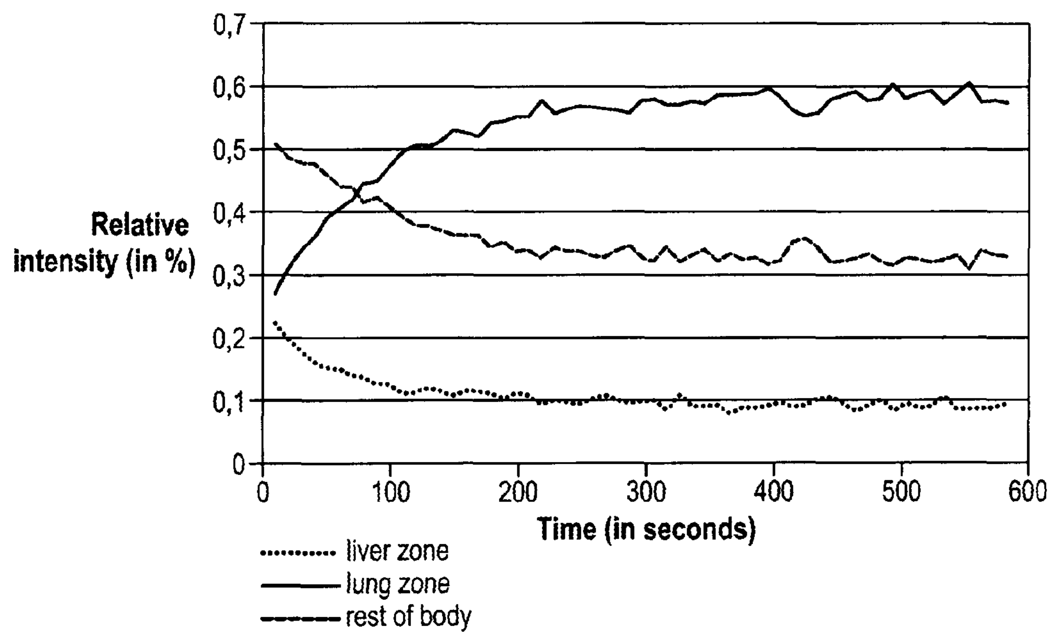
FIG. 8: Dynamics of $ZnMgSi_2O_6$ nanoparticles doped with Eu, Mn, Dy after intravenous injection
Figure 9:
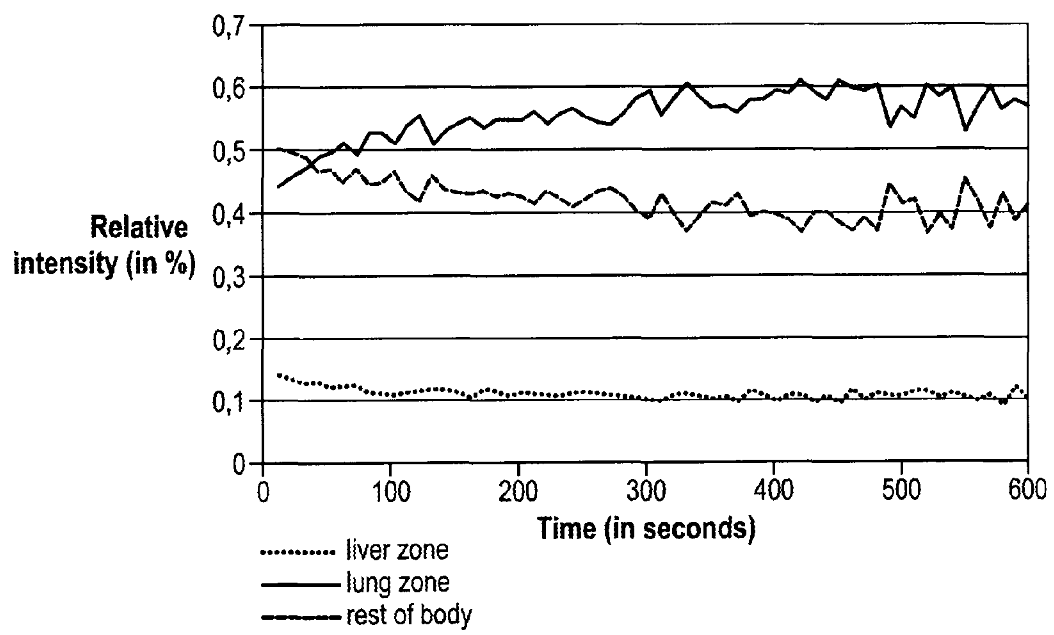
FIG. 9: Dynamics of $ZnMgSi_2O_6$ nanoparticles doped with Eu, Mn, Dy coated with methoxy-$PEG_{5000}$ after intravenous injection
Figure 10:
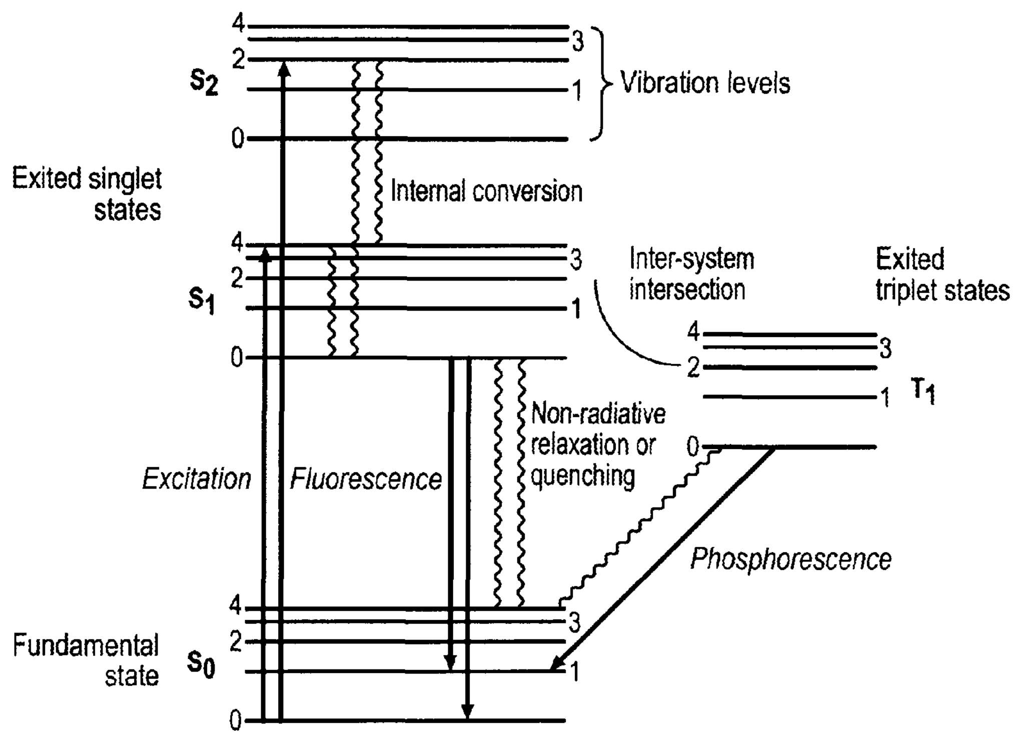
FIG. 10: Jablonski diagram
Figure 11:
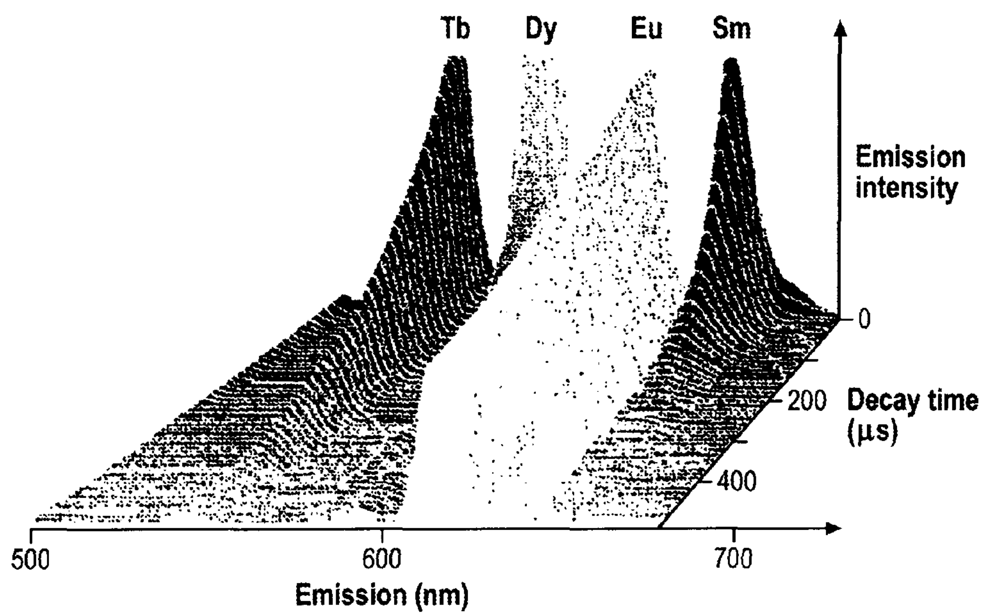
FIG. 11: Luminescence spectra and lifetimes of lanthanide chelates proposed in the Perkin Elmer DELFIA® system.
Figure 12:
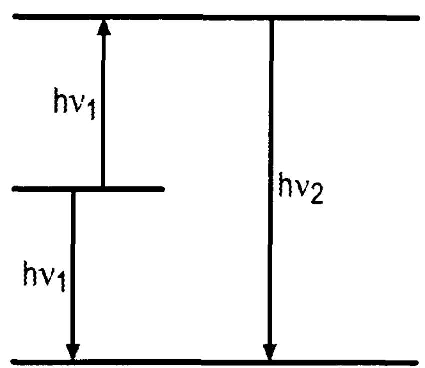
FIG. 12: Diagram explaining the upconversion phenomenon in materials
Figure 13:
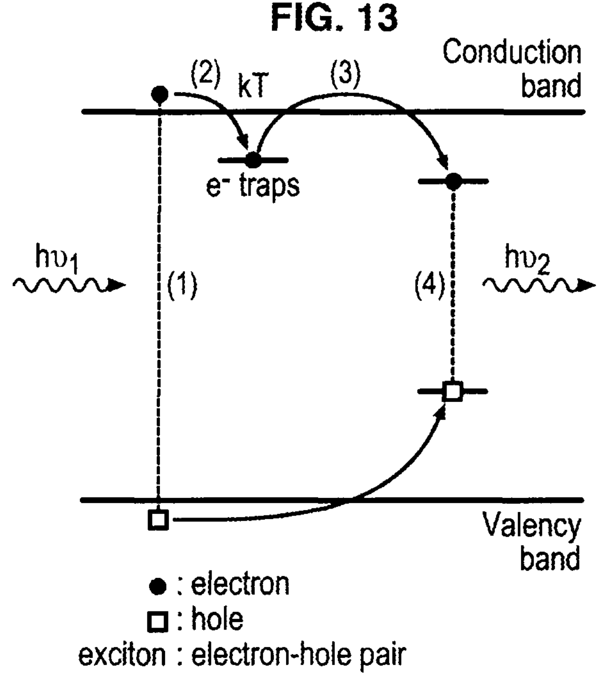
FIG. 13: Simplified persistent luminescence diagram in materials

FIG. 8 gives an indication of the in vivo particle dynamics of the particles not coated with PEG after intravenous injection. FIG. 9 shows the different behavior which PEG grafting has been performed on the surface of the nanoparticles. Indeed, very low retention in the lungs and an increase in luminescence from zones other than the liver and lungs are observed.

Example 5

New $Ca_{0.2}Zn_{0.9}Mg_{0.9}Si_2O_6$ Compound Doped with $Eu^{2+}$, $Dy^{3+}$, $Mn^{2+}$ In order to optimize emission in the infrared spectrum and the nanoparticle preparation, the inventors selected the material $Ca_{0.2}Zn_{0.9}Mg_{0.9}Si_2O_6$ doped with $Eu^{2+}$, $Dy^{3+}$, $Mn^{2+}$. The characteristics of this material are shown in FIG. 14.

Figure 14A:
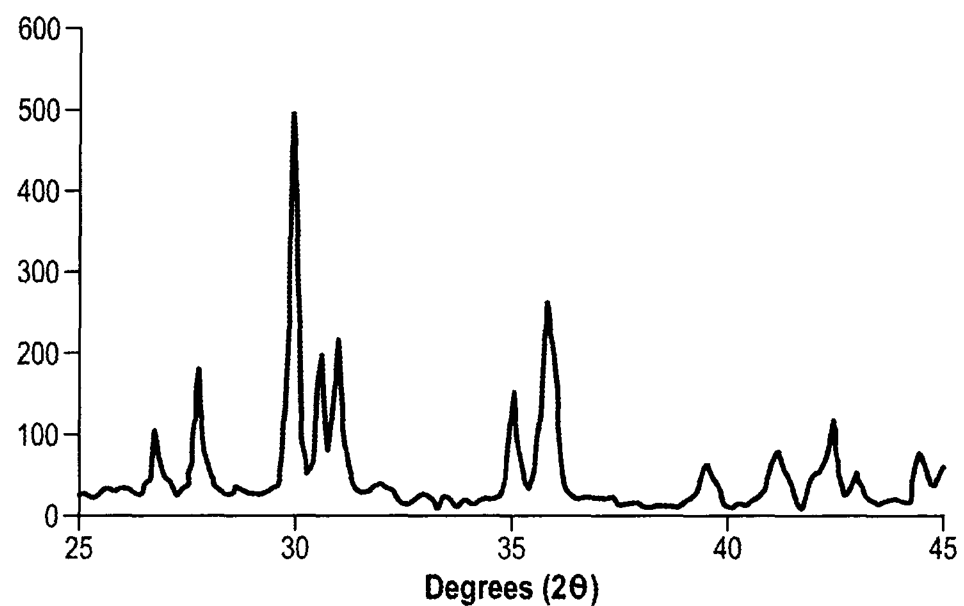
FIG. 14: Properties of $Ca_{0.2}Zn_{0.9}Mg_{0.9}Si_2O_6$ nanoparticles doped with $Eu^{2+}$ (0.5%), $Dy^{3+}$ (1.0%), $Mn^{2+}$ (2.5%).
Figure 14B:
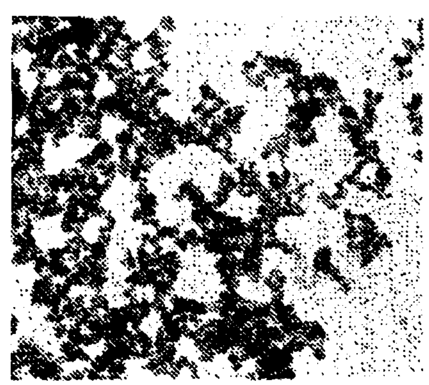
Figure 14C:
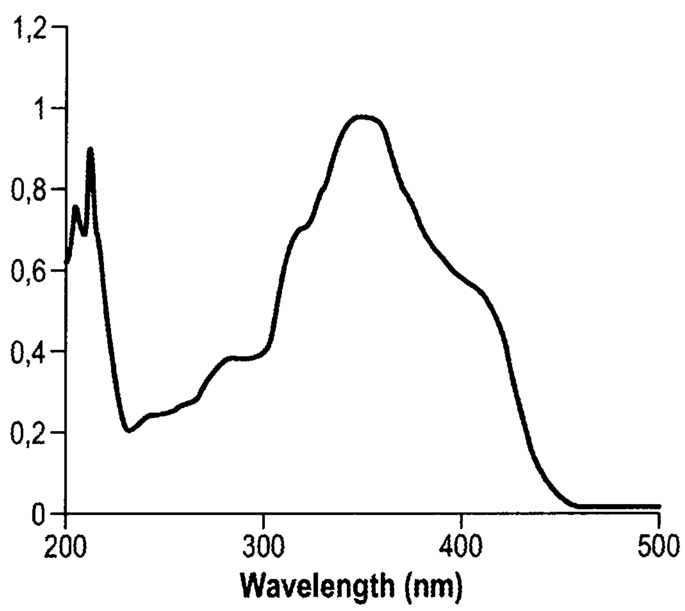
Figure 14D:
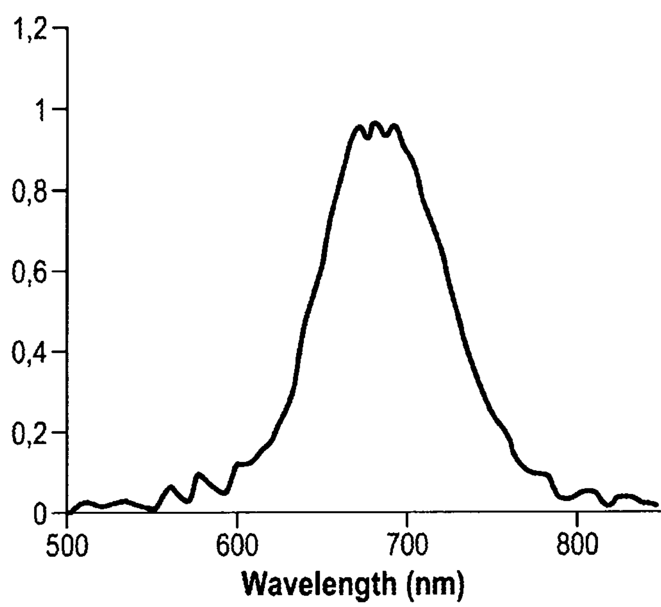
Figure 14E:
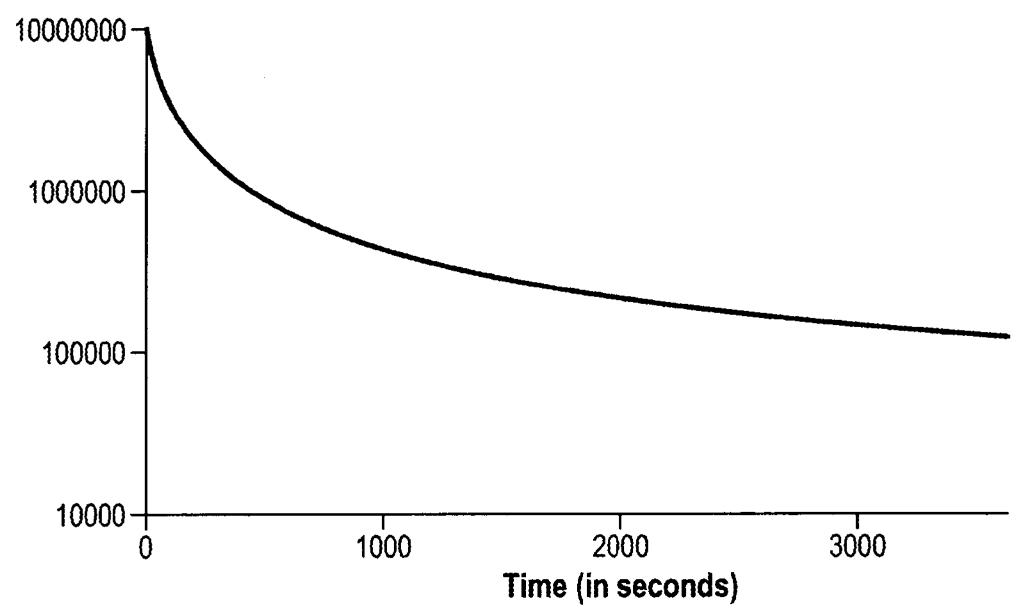

The persistent luminescence materials are generally synthesized by solid process, this technique producing particles of a micrometric size. A Sol-Gel process approach was developed to reduce the size of the particles. Briefly, to an acidified water solution at pH~2, the various salts are added in the desired proportions (zinc chloride, calcium chloride, magnesium nitrate, europium chloride, dysprosium chloride and manganese chloride for the compound $Ca_{0.2}Zn_{0.9}Mg_{0.9}Si_2O_6$ doped with $Eu^{2+}$, $Dy^{3+}$, $Mn^{2+}$). After dissolution of the salts, tetraethoxysilane (TEOS) is added rapidly. The solution is placed under stirring until the solution becomes clear. This is due to the hydrolysis of the TEOS. The transparent solution is then heated to 70° C. until it gels. The gel is then dried at 110° C. for approximately 20 hours and calcined at 1050° C. for 10 hours in a reducing atmosphere in order to reduce $Eu^{3+}$ to $Eu^{2+}$. This reduction is essential to obtain the persistent luminescence property in this material. The crystalline material (FIG. 14A) obtained is then ground using a mortar and pestle. The smallest particles are then selected by means of selective sedimentation. An electron microscopy analysis demonstrated that the nanoparticles (NPs) displayed a relatively homogeneous size with a particle diameter between 50 and 100 nm (FIG. 14B).

In this material, the traps are created by introducing a small quantity of $Dy^{3+}$, while $Mn^{2+}$ is the emitting center, receiving the energy from the electron-hole recombinations. The rare earth ions serve as the primary acceptor of energy, which is released in the form of heat and transmitted to the manganese for several hours. The symmetry and the crystalline field around $Mn^{2+}$ is responsible for the emission in the red and near infrared spectrum from the manganese in the synthesized compound. This emission corresponds to the transition from the excited state $^4T_1(^4G)$ to the fundamental state $^6A_1$ ($^6S$). As demonstrated in FIG. 14D, the persistent luminescence emission spectrum is relatively wide, with an intensity peak around 690 nm. This emission band is of particular interest as it is located in the tissue transparency zone. As the wide excitation band in the UV (FIG. 14C) cannot be solely attributed to the absorption bands of manganese, the persistent luminescence observed is indeed due to energy transfer within the material. This characteristic of wide excitation bands in the UV enables the use of laboratory UV lamps for the excitation of the nanoparticles.

For the acquisition of the signal after the suppression of the excitation source, a CCD ("charged coupled device") type detector may be used (PhotonImager, Biospace) without an external illumination system. When the nanoparticles are kept in the dark, the decline in light intensity is typical of a persistent luminescence material and persists for over 24 hours. The decline kinetics (FIG. 14E) may be approximated by a power law $I \sim I \times t^{-n}$ (n=0.96, $R^2$=0.996) for times of more than 100 s. To the knowledge of the inventors, this is the first time that particles having spectral properties and these nanometric sizes are synthesized.

The inventors did not find any use of persistent luminescence compounds for in vivo imaging. They firstly demonstrated that the luminescence level produced by the nanoparticles after the end of the excitation was sufficient to give rise to a localizable signal in a few mm of tissues, as in subcutaneous or intramuscular injection experiments. In this way, a nanoparticle suspension was injected subcutaneously into the back of a not previously shaven Swiss mouse. For the excitation before injection, the suspended nanoparticles were exposed directly to a 6 Watt UV lamp for 5 min at a distance of 2 cm (FIG. 15). In order to test the lowest detectable dose, 20 μl of suspensions at different nanoparticle concentrations (100, 10, 1 μg/ml) were injected at three different points on the back of the mouse. The highest doses (corresponding to 2 μg and 200 ng of nanoparticles, respectively) were detected easily. The lowest dose administered (20 ng) also gave a detectable signal with a satisfactory signal-to-noise ratio as it was greater than 5.

In order to confirm the feasibility of deep tissue imaging, an injection in the cranial tibial muscle of a Swiss mouse was performed with a larger quantity of nanoparticles (20 μl at a concentration of 10 mg/ml of nanoparticles). The signal was clearly detectable and defined the contour of the muscle of the mouse. While the injection carried out was at an individual point, the signal observed was diffuse throughout the muscle. By eliminating the need for in situ illumination, the use of persistent luminescence nanoparticles thus makes it possible to observe light diffusion in tissues simply. A signal from the animal's leg was also observed, while no nanoparticles had been injected therein. This was attributed to the reflection of the signal from the muscle onto the mouse's leg.

Figure 16:
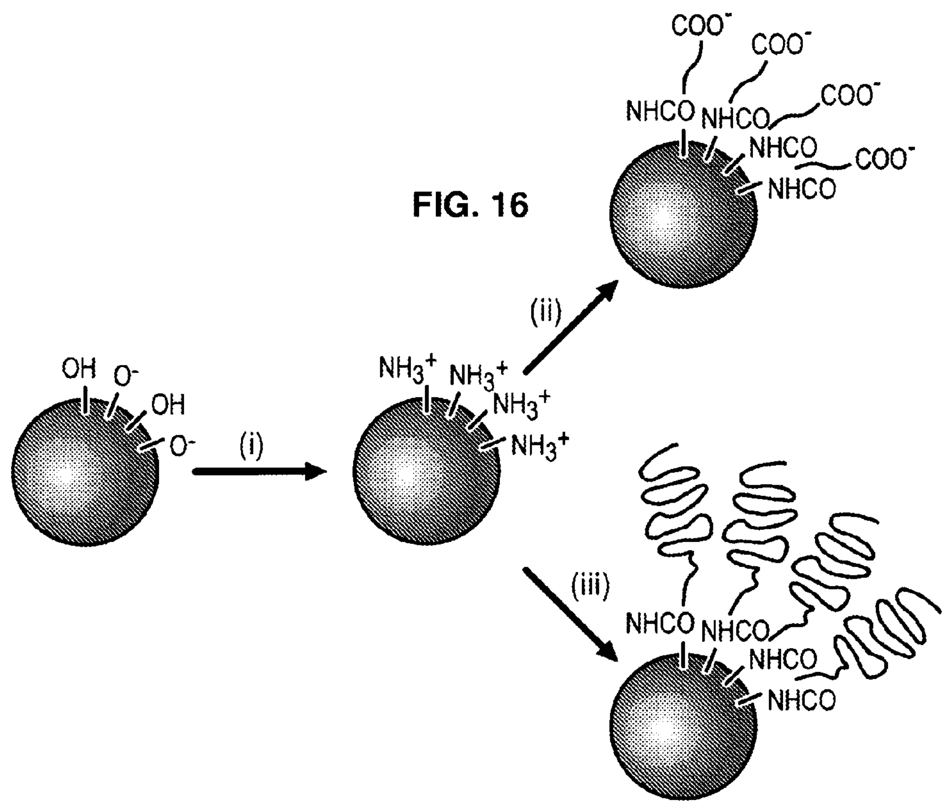

In order to ensure success and broaden the scope, it must be possible for the optical probes to be functionalized. Coating techniques conventionally used for silicates were used (FIG. 16). After heat treatment, hydroxyl groups are created on the surface of the nanoparticles by means of partial erosion of the surface by a base (NaOH, 5 mM). These hydroxyls give the nanoparticles a negative Zeta potential at neutral pH (−34.3 mV) and enable the covalent grafting of different functional groups. The nanoparticles are then dispersed in dimethylformamide to react with 3-aminopropyltriethoxysilane (APTES) which will be grafted covalently to the surface of the nanoparticles. This results in positively charged nanoparticles due to the presence of free amine groups on the surface of the nanoparticles. These particles will be referred to as amino-NPs. The success of the grafting was monitored by measuring the Zeta potential of the amino-NPs (+35.8 mV at pH~7) and by a positive test for trinitrobenzene sulfonate (TNBS). The excess APTES was removed by successive sedimentation-washing steps.

The amino-NP surface load was inverted by means of a reaction with diglycol anhydride, which reacts with free amines. This reaction thus makes it possible to obtain carboxyl groups on the surface of the nanoparticles. The Zeta potential of these nanoparticles (referred to as carboxy-NPs) was as expected negative at neutral pH (−37.3 mV). Peptide coupling using $mPEG_{5000}$-COOH (α-carboxy-ω-methoxy-polyethyleneglycol F.W.: ~5000 g/mol) was performed on the amines of the amino-NPs. This makes it possible to obtain neutral particles (Zeta potential of +5.1 mV at neutral pH) which will be referred to as PEG-NPs. Each time, all the products which had not reacted were removed by means of sedimentation-washing steps. Three types of nanoparticles carrying different surface loads were thus obtained.

Even if it is known that the surface load influences in vivo particle distribution, biodistribution monitoring is not generally performed in real-time. For example, the animals must be sacrificed at different times to determine the biodistribution kinetics of liposomes or nanoparticles. The biodistribution of the different types of persistent luminescence nanoparticles was monitored by means of real-time optical imaging on mice following the injection of 1 mg of nanoparticles (corresponding to $10^{13}$ nanoparticles) into the tail vein.

For positively charged amino-NPS, significant retention was observed in the lungs. During the first hour, the biodistribution of the nanoparticles did not change much, with simply a progressive but slow transfer of the nanoparticles from the lungs to the liver and the spleen. Two reasons may explain this sequestration tendency in the lungs. The first is the non-specific electrostatic interaction of the nanoparticles with negative proteins covering the surface of the endothelial cells, such as for example, glycosaminoglycans. Indeed, the lungs are the first highly vascularized organ encountered by the nanoparticles after systemic injection into a mouse's tail vein. As the blood flow is lower due to the circulation in the capillaries, non-specific interactions become significant with respect to the other interactions and thus block the amino-NPs in the lungs. Another explanation may stem from the aggregation of the nanoparticles with negatively charged compounds in the blood thus preventing satisfactory circulation in the capillaries of the lungs and thus inducing the sequestration thereof.

For negatively-charged carboxy-NPs, no pulmonary sequestration was observed. This is probably due to the fact that the negative nanoparticles do not interact with the endothelial cells of the lungs and thus remain in the blood circulation for longer than positive particles. However, high liver uptake was observed. This is probably the result of opsonization and uptake of the nanoparticles by endothelial cells and Kupffer cells in the reticuloendothelial system (RES).

It has been demonstrated by several authors that the use of PEG covering the surface of nanoparticles made it possible to reduce rapid blood circulation elimination. In this way, the PEG-NPs confirmed this tendency as the signal obtained after injection was diffuse and covered the entire body of the mouse, for the entire experiment (45 min). However, after 30 min, an accumulation in the reticuloendothelial system was observed.

The uptake of exogenous compounds by the liver or spleen is an evident problem that needs to be resolved to target other tissues, such as tumors.

Some authors have described techniques making it possible to eliminate or minimize uptake by the RES. Of these techniques, the use of anionic liposomes containing an equimolar quantity of phosphatidylcholine, cholesterol and phosphatidylserine makes it possible to saturate the RES and thus extend the lifetime of the injected compounds in the blood circulation. The liposomes were prepared by hydrating a film of lipids and extruded in order to obtain negative liposomes (Zeta potential—43.3 mV) with a diameter of approximately 300 nm.

By reducing the number of potential interaction sites, an intravenous pre-injection of anionic liposomes (6 μmol, 100 μl injected for 5 min before the injection of nanoparticles) made it possible to increase the circulation time of negatively charged carboxy-NPs considerably in mice, even though these particles were eventually localized in the liver and spleen.

The effect of a pre-injection of anionic liposomes had an even greater effect on the PEG-NP circulation time. The signal obtained was in fact diffuse throughout the experiment thus demonstrating the presence of the nanoparticles in the vasculature of the mouse. It should be noted that the femoral arteries and the carotids were viewed. After 15 min, the contour of the spleen was clearly visible while 30 min were required for the contour of the liver to emerge from the peripheral circulation of the upper body of the mouse.

In this way, even though the pre-injection of compounds with the RES does not alter the final biodistribution of the nanoparticles, it improves the circulation time of the nanoparticles significantly and thus the possibility of obtaining specific targeting of the nanoparticles.

Figure 17:
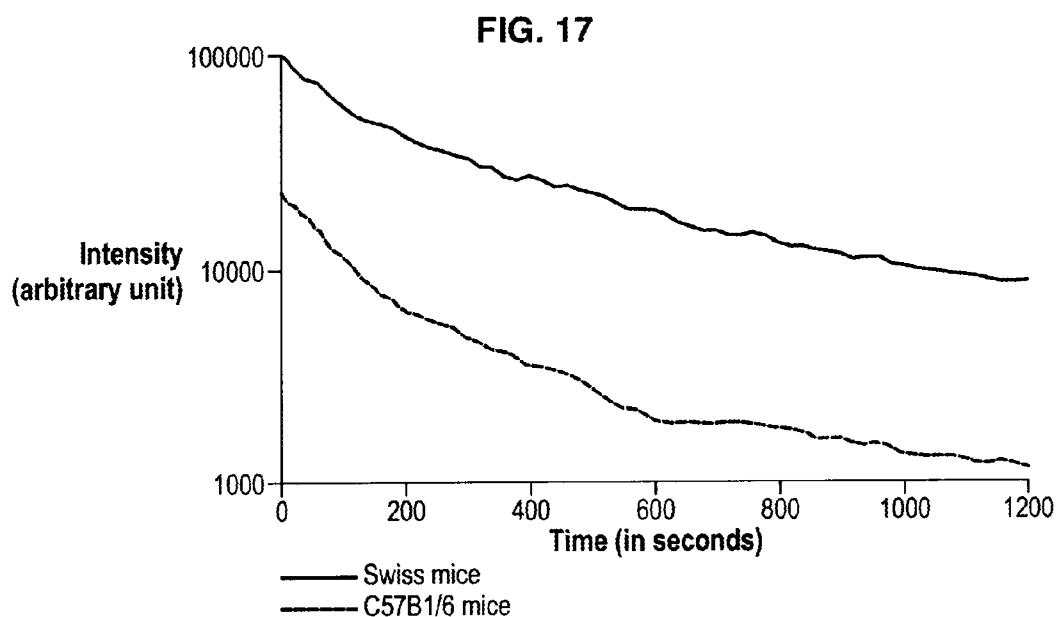

Finally, the extensive vascularization of a tumor was detected using persistent luminescence nanoparticles. Lewis lung carcinoma (3LL) was implanted in the inguinal region of a C57B1/6 mouse. The previously shaven mouse was injected with PEG-NPs (1 mg) 5 min after the injection of anionic liposomes (6 μmol, 100 μl). The presence of melanin in the skin of C57B1/6 mice is particularly unfavorable for conducting in vivo optical imaging experiments. In face, the melanin attenuation coefficient is very high and covers the entire visible spectrum. In this way, the total intensity detected was significantly lower (by a factor of 5 to 7) compared to that obtained for a Swiss mouse (FIG. 17). However, the use of persistent luminescence nanoparticles made it possible to obtain an easily detectable signal and the biodistribution of the nanoparticles was monitored by means of optical measurement. In this way, the tumoral region was detected by increasing the light intensity at this point. This increase is attributed to the extensive vascularization of a 3LL tumor.

Synthesis of the Nanoparticles of the Compound $Ca_{0.2}Zn_{0.9}Mg_{0.9}Si_2O_6$ Doped with $Eu^{2+}$ (0.5%), $Dy^{3+}$ (1.0%), $Mn^{2+}$ (2.5%)

The chemical products used to synthesize the nanoparticles are magnesium nitrate ($Mg(NO_3)_2$, $6H_2O$), zinc chloride ($ZnCl_2$), calcium chloride ($CaCl_2$, $2H_2O$), europium chloride ($EuCl_3$, $6H_2O$), dysprosium nitrate ($Dy(NO_3)_3$, $5H_2O$), manganese chloride ($MnCl_2$, $4H_2O$) and tetraethoxysilane (TEOS). All the salts are dissolved in acidified water at pH 2 by adding concentrated nitric acid. TEOS is then added rapidly and the solution is stirred vigorously at ambient temperature until a clear solution is obtained (approximately 1 hour). The solution is then heated to 70° C. until it gels (approximately 2 hours). The wet gel is then dried in an oven at 110° C. for 20 hours. The opaque gel obtained is calcined directly in a zirconium crucible in a reducing atmosphere (Noxal 4: 10% $H_2$, 90% Ar) at 1050° C. for 10 hours. The material obtain is then ground in a mortar to obtain the desired nanoparticles.

The powder is dispersed by sonication in a soda (5 mM) solution at a concentration of 10 mg of nanoparticles per ml. After neutralization with a hydrochloric acid solution, the suspension is diluted with distilled water until a suspension at a concentration of 2.5 mg of nanoparticles per ml is obtained. This suspension is then centrifuged using a SANYO MSE Mistral 1000 centrifuge (2000 rpm for 15 min) in order to eliminate the largest particles. To the supernatant, 25% by volume of acetone is added. This makes it possible to facilitate the sedimentation of the nanoparticles during centrifugation at 4500 rpm for 30 min which makes it possible to retrieve the smallest particles. After removing the supernatant, the sediment consisting of the nanoparticles is retrieved. The nanoparticles are then dried in an oven in a vacuum.

Other Surface Modification Method

Example of functionalization for the compound $Ca_{0.2}Zn_{0.9}Mg_{0.9}Si_2O_6$ doped with $Eu^{2+}$ (0.5%), $Dy^{3+}$ (1.0%), $Mn^{2+}$ (2.5%)

In order to obtain the amino-NPs, 100 mg of nanoparticles are dispersed in 10 ml of dimethylformamide (DMF) and 50 μl of 3-aminopropyl-triethoxysilane (APTES) is added under stirring. The suspension is then stirred overnight at 80° C. After reaction, several series of centrifugations and redispersions in DMF make it possible to wash the excess APTES.

In order to obtain the carboxy-NPs, 52.8 mg of amino-NPs are redispersed in DMF and diglycol anhydride (12.2 mg, 0.11 mmol) is added. The suspension is then stirred overnight at ambient temperature. After the reaction, the excess reagents are removed by means of successive washes.

In order to obtain the PEG-NPs, 53.4 mg of amino-NPs are redispersed in 10 ml of DMF in the presence of Methoxy-$PEG_{5000}$-COOH (534 mg, 0.11 mmol), benzotriazol-1-yl-oxy-tris(dimethylamino)-phosphonium hexafluorophosphate (BOP reagent, 52 mg, 0.12 mmol) and triethylamine (15 μl). The excess reagents are removed by means of successive washes.

Anionic Liposome Synthesis

Phosphatidylcholine (11.78 mg, 15.5 μmol), cholesterol (5.99 mg, 15.5 μmol) and L-phosphatidylserine (12.2 mg, 15.5 μmol) are dissolved in 1 ml of chloroform. After eliminating the solvent by means of vacuum evaporation, the lipid film obtained is hydrated at 37° C. overnight with 1.935 ml of 10 mM PBS. The suspension is then extruded via 0.4 μm filters using a mini-extruder (Avanti Polar Lipids). Before injection, the liposome suspension is diluted with 10 mM PBS in order to obtain an anionic liposome suspension at a lipid concentration of 6 mM.

Analysis of Data for a Subcutaneous Injection

For the lowest dose (20 ng), the signal intensity was greater than 10 while the background noise signal has a mean intensity of 2.5 with a variance of 1.5. The signal-to-noise ratio is calculated as the ratio between the amplitude of the signal (~7.5) and the variance of the noise (1.5) is therefore greater than 5 (see FIG. 18).

Qualitative Evaluation of Nanoparticle Circulation Time

In order to evaluate the circulation time of the nanoparticles (NPs), a region of interest (ROI) covering the lungs, liver and the region of the spleen (ROI_1) was selected manually and analyzed by 20 s periods. The intensity was then divided by the total light intensity of the body (ROI_2) detected by each mouse.

In this way, the blood concentration of the nanoparticles is associated with the function $F(t)=1-ROI\_1/ROI\_2$.

As described in FIG. 19, for the amino-NPs, the percentage of luminescence in the RES-lung region is high (75%) one second after the injection and practically does not fluctuate. For the carboxy-NPs, the curve declines rapidly from 0.5 to 0.2 in approximately 10 min, and the pre-injection of anionic liposomes increases the initial level to 0.65. The circulation time is also extended in view of the time required to obtain similar levels when the NPs are injected on their own. For PEG-NPs, the initial level is high (0.65). The curve declines more slowly and the level is finally 0.4 after 1 hour. This level is lower than for the other type of NPs resulting from the "stealth effect" of the PEG range on the circulation time. The pre-injection of liposome before the PEG-NP injection enables long-term NP circulation.

Long-Term Monitoring Experiments

The following experiment was conducted to determine whether the nanoparticles could be eliminated on a more long-term basis.

A group of 30 Swiss mice received, on the same day, an i.v. injection with a suspension of non-functionalized nanoparticles (1 mg per mouse). The control group was injected with physiological saline solution.

No mice died following the injection. A slight weight loss in the injected group compared to the control group was observed during the first days. However, at the longer time, both groups were of a similar weight (FIG. 20). This would tend to demonstrate that the nanoparticles do not have an acute toxicity effect on mice. More precise studies with repeated injections should be conducted to understand the toxicity of the nanoparticles more clearly.

In order to determine whether the nanoparticles could be eliminated, the mice were sacrificed in groups of 4, their organs were removed (liver, spleen, kidneys and lungs) and the quantity of nanoparticles assayed in each organ.

The results of this analysis demonstrated that the quantity of nanoparticles was, as expected, largely higher in the liver than on the other organs (see FIG. 21-24). The inventors observed during the first days an increase in the number of nanoparticles in the liver, demonstrating the uptake mechanism by the liver. At the long time, the trend reversed with less and less particles present in all the organs. At the time M6 (6 months after the injection), the quantity of nanoparticles detected in the organs was practically inexistent.

In the inventors' view, the particles may be eliminated by the biliary tract.

Viewing of Tumors in Mice:

The inventors wished to know whether the nanoparticles were capable of detecting the location of a tumor implanted on mice. Two types of tumors were used: a tumor from a case of Lewis lung carcinoma (3LL) and a B16 melanoma type tumor.

One of the specificities of the 3LL tumors is extensive vascularization. In this way, an increase in the signal on the tumor is observed, which makes it possible to distinguish the contour of the tumor clearly. B16 tumors, from melanoma, contain a high quantity of melanin, a pigment that absorbs light significantly. In this way, the tumor was in this case detected by an absence of a signal from the tumor.

Experiments on Rats:

The inventors wished to determine whether the light emitted by the nanoparticles was sufficient to perform imaging on larger animals than mice.

Therefore, they tested whether it was possible to conduct monitoring of nanoparticles following systemic injection on a Wistar rat (300 g). As a comparison, the weight of a mouse varies from 20 to 30 g.

Therefore, a quantity of particles equivalent to those used for the mice (1 mg) was injected intravenously via the tail vein. Rapid liver uptake was thus detected in rats.

The invention claimed is:

1. Method for in vivo optical imaging of an organism comprising the steps of:

a) providing a persistent luminescence nanoparticle, between 25 nm and 1 μm in size, emitting photons at wavelengths between 600 and 1300 nm for at least one minute to several hours, after light excitation at wavelengths between 100 and 800 nm, or after excitation by means of X-rays, wherein said nanoparticle consists of a compound selected from the group consisting of: silicates, aluminates, aluminosilicates, germanates, titanates, oxysulfides, phosphates and vanadates, such compounds comprising at least one metal oxide, sulfides comprising at least one metal ion selected from zinc, strontium and calcium, and metal oxides, said compound being doped with at least one rare earth ion, and optionally with at least one transition metal ion;

b) exciting said persistent luminescence nanoparticle by means of light excitation at wavelengths between 100 and 800 nm or by means of X-rays;

c) administering the excited persistent luminescence nanoparticle obtained in step b) to the organism under study;

d) detecting said persistent luminescence nanoparticle in vivo at wavelengths between 600 and 1300 nm to obtain an in vivo optical image of said organism.

2. Method for in vivo optical imaging of an organism according to claim 1, wherein the nanoparticle is between 50 nm and 500 nm in size.

3. Method for in vivo optical imaging of an organism according to claim 1, wherein the metal of the metal oxide is selected from magnesium, calcium, strontium, barium, zinc, cadmium, yttrium and gallium.

4. Method for in vivo optical imaging of an organism according to claim 1, wherein the rare earth ion is selected from europium, ytterbium, cerium, samarium, praseodymium, dysprosium, neodymium, holmium, terbium, thulium and erbium ions.

5. Method for in vivo optical imaging of an organism according to claim 1, wherein the transition metal is selected from manganese, chromium and titanium.

6. Method for in vivo optical imaging of an organism according to claim 1, wherein the nanoparticle consists of a silicate comprising a metal oxide doped with at least one rare earth ion and at least one transition metal ion.

7. Method for in vivo optical imaging of an organism according to claim 1, wherein the nanoparticle consists of a compound selected from the group consisting of the silicates $ZnMgSi_2O_6$, $CaMgSi_2O_6$ and $MgSiO_3$, said silicates being doped with manganese, europium and dysprosium ions, and $Sr_2MgSi_2O_7$ doped with europium and dysprosium ions.

8. Method for in vivo optical imaging of an organism according to claim 1, wherein the nanoparticle consists of the silicate $Ca_{0.2}Zn_{0.9}Mg_{0.9}Si_2O_6$ doped with $Eu^{2+}$, $Dy^{3+}$, $Mn^{2+}$.

9. Method for in vivo optical imaging of an organism according to claim 1, wherein the nanoparticle is functionalized by coating and/or grafting a ligand enabling bonding with a substance of biological or chemical interest.

10. Method for in vivo optical imaging of an organism according to claim 1; wherein the in vivo optical imaging is for imaging the vascularization of the body.

11. Method for in vivo optical imaging of an organism according to claim 1, wherein the in vivo optical imaging is for the imaging of tumoral, inflammatory or retinal zones, said zones being liable to be hypervascularized, or blood-brain barrier rupture zones.

12. Method for in vivo optical imaging of an organism according to claim 1, wherein the in vivo optical imaging is for the imaging of hypovascularized zones such as in the case of cerebral or cardiac ischemia, or in the case of cranial trauma.

* * * * *